(12) United States Patent
Griebel et al.

(10) Patent No.: US 8,685,322 B2
(45) Date of Patent: Apr. 1, 2014

(54) APPARATUS AND METHOD FOR THE PURIFICATION OF BIOMOLECULES

(75) Inventors: Ralf Griebel, Birkenfeld (DE); Hans Joos, Berlin (DE); Peter Bendzko, Berlin (DE)

(73) Assignee: STRATEC Biomedical AG, Birkenfeld (DE)

( * ) Notice: Subject to any disclaimer, the term of this patent is extended or adjusted under 35 U.S.C. 154(b) by 393 days.

(21) Appl. No.: 12/270,621

(22) Filed: Nov. 13, 2008

(65) Prior Publication Data
US 2009/0176308 A1 Jul. 9, 2009

(30) Foreign Application Priority Data

Nov. 13, 2007 (DE) .................. 10 2007 054 033

(51) Int. Cl.
*G01N 35/02* (2006.01)
*G01N 35/10* (2006.01)

(52) U.S. Cl.
USPC .............................................. 422/67; 422/63

(58) Field of Classification Search
None
See application file for complete search history.

(56) References Cited

U.S. PATENT DOCUMENTS

| | | | |
|---|---|---|---|
| 5,567,326 A | 10/1996 | Ekenberg et al. | |
| 5,705,062 A | 1/1998 | Knobel | |
| 5,705,628 A * | 1/1998 | Hawkins | 536/25.4 |
| 6,037,465 A | 3/2000 | Hillebrand et al. | |
| 6,040,192 A | 3/2000 | Tuunanen | |
| 6,110,363 A | 8/2000 | Hillebrand et al. | |
| 6,409,925 B1 | 6/2002 | Gombinsky et al. | |
| 6,448,092 B1 | 9/2002 | Tuunanen | |
| 6,596,162 B2 | 7/2003 | Tuunanen | |

(Continued)

FOREIGN PATENT DOCUMENTS

| | | | |
|---|---|---|---|
| CA | 2315064 A | 7/1999 | |
| DE | 44 22 044 A | 12/1995 | |

(Continued)

OTHER PUBLICATIONS

Bowman, Barbara H. et al. "Rapid production of single-stranded sequencing template from amplified DNA using magnetic beads." Methods in Enzymology (1993) 224 p. 399-406.*

(Continued)

*Primary Examiner* — Christopher A Hixson
(74) *Attorney, Agent, or Firm* — Hultquist, PLLC; Steven J. Hultquist

(57) ABSTRACT

The invention comprises an apparatus 10 and a method 100 for purifying biomolecules 28. Magnetizable particles 35 and a group of magnetizable pins 40 are used for binding biomolecules 28 to the magnetizable particles 35 using a binding buffer 30*b*, and for transferring the magnetizable particles 35 forming a particle-biomolecule complex 36. The apparatus 10 comprises an incubation unit 60 that allows for an upscaling of a maximum volume of a sample material. Furthermore the apparatus 10 comprises counter magnets 50 which are arranged on cavities 20. Solutions 30 comprising the biomolecules 28 and the magnetizable particles 35 are disposed in the cavities. The use of counter magnets 50 improves the quality of an eluate. Furthermore the invention comprises a system 800 and a method 900 for a diagnostically purifying of biomolecules 28. The method 900 further comprises a controlling of method steps and a selection of substances and reagents (for example the magnetizable particles 35) based on information automatically collected from, for example, the samples and/or derived from used substances and reagents. The system 800 fulfills requirements of medical diagnostics.

15 Claims, 19 Drawing Sheets

(56) References Cited

U.S. PATENT DOCUMENTS

Figure 1B:
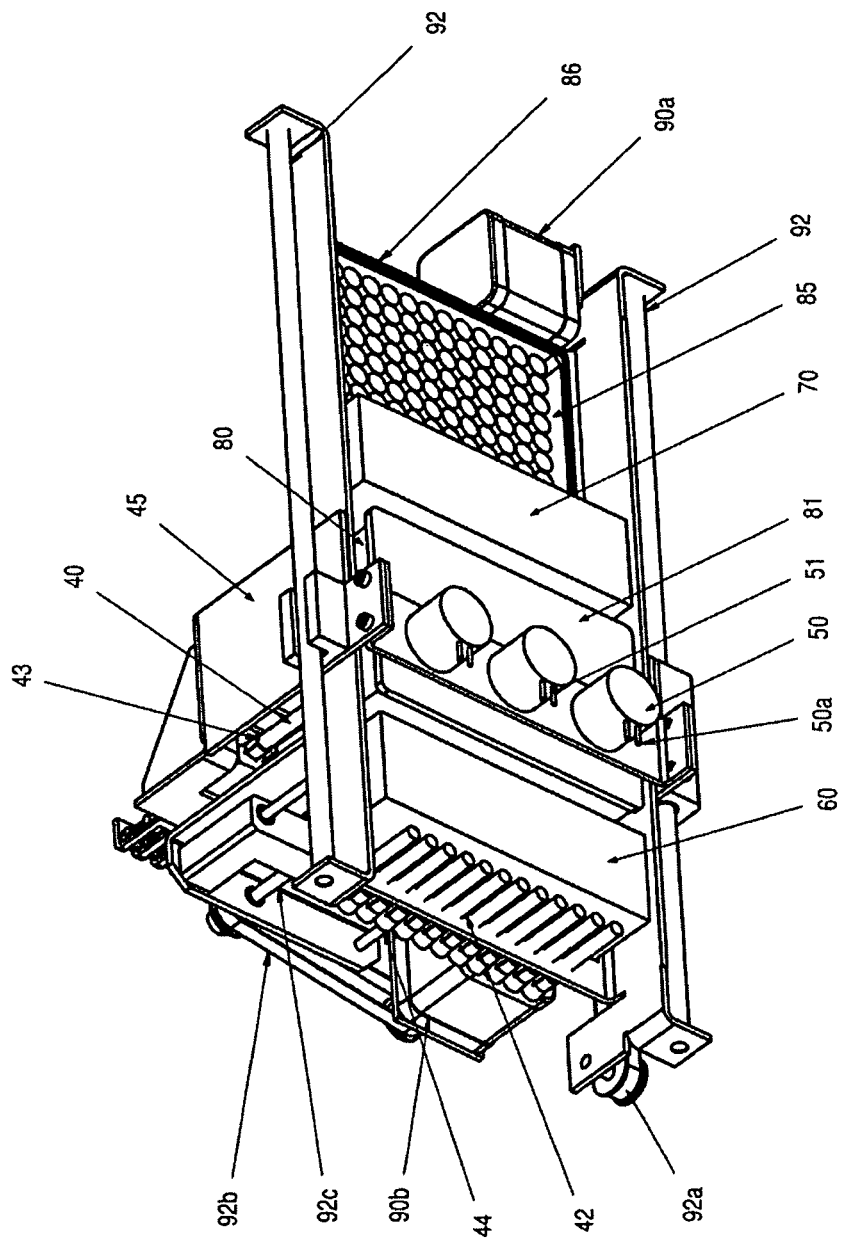

| | | |
|---|---|---|
| 6,605,213 B1 | 8/2003 | Ammann et al. |
| 6,943,029 B2 * | 9/2005 | Copeland et al. ............... 436/46 |
| 2001/0041332 A1 | 11/2001 | Hillebrand et al. |
| 2003/0152961 A1 | 8/2003 | Bendzko et al. |
| 2004/0134750 A1 * | 7/2004 | Luoma, II ..................... 198/340 |
| 2005/0013741 A1 | 1/2005 | a'Brassard |
| 2006/0160085 A1 | 7/2006 | Hillebrand et al. |
| 2006/0266130 A1 * | 11/2006 | Zobel et al. ................. 73/864.02 |
| 2007/0214900 A1 | 9/2007 | Porat et al. |
| 2007/0218566 A1 | 9/2007 | Barten et al. |
| 2009/0176308 A1 | 7/2009 | Greibel et al. |

FOREIGN PATENT DOCUMENTS

| | | |
|---|---|---|
| DE | 198 56 064 C2 | 6/2000 |
| DE | 10111520 A1 | 1/2003 |
| DE | 10 253 351 A1 | 5/2004 |
| EP | 0644425 A1 | 9/1994 |
| EP | 0880535 B1 | 7/1996 |
| EP | 0681700 B1 | 11/2001 |
| EP | 1726963 A2 | 11/2006 |
| WO | 9609550 A1 | 3/1996 |
| WO | 9612958 A1 | 5/1996 |
| WO | 9932616 A2 | 7/1999 |
| WO | 9940444 A1 | 8/1999 |
| WO | 0034463 A1 | 6/2000 |
| WO | 0170386 A2 | 9/2001 |
| WO | 03044537 A1 | 5/2003 |
| WO | 2004042058 A2 | 5/2004 |
| WO | 2005050208 A2 | 6/2005 |
| WO | 2007020294 A1 | 2/2007 |

OTHER PUBLICATIONS

Hanley, Robert et al. "DNA integrety assay: a plasma-based screening tool for the detection of prostate cancer." Clinical Cancer Research (2006) 12 p. 4569-4574.*

Klaenhammer, Todd R. "A general method for plamid isolation in lactobacilli." Current Microbiology (1984) p. 23-28.*

* cited by examiner

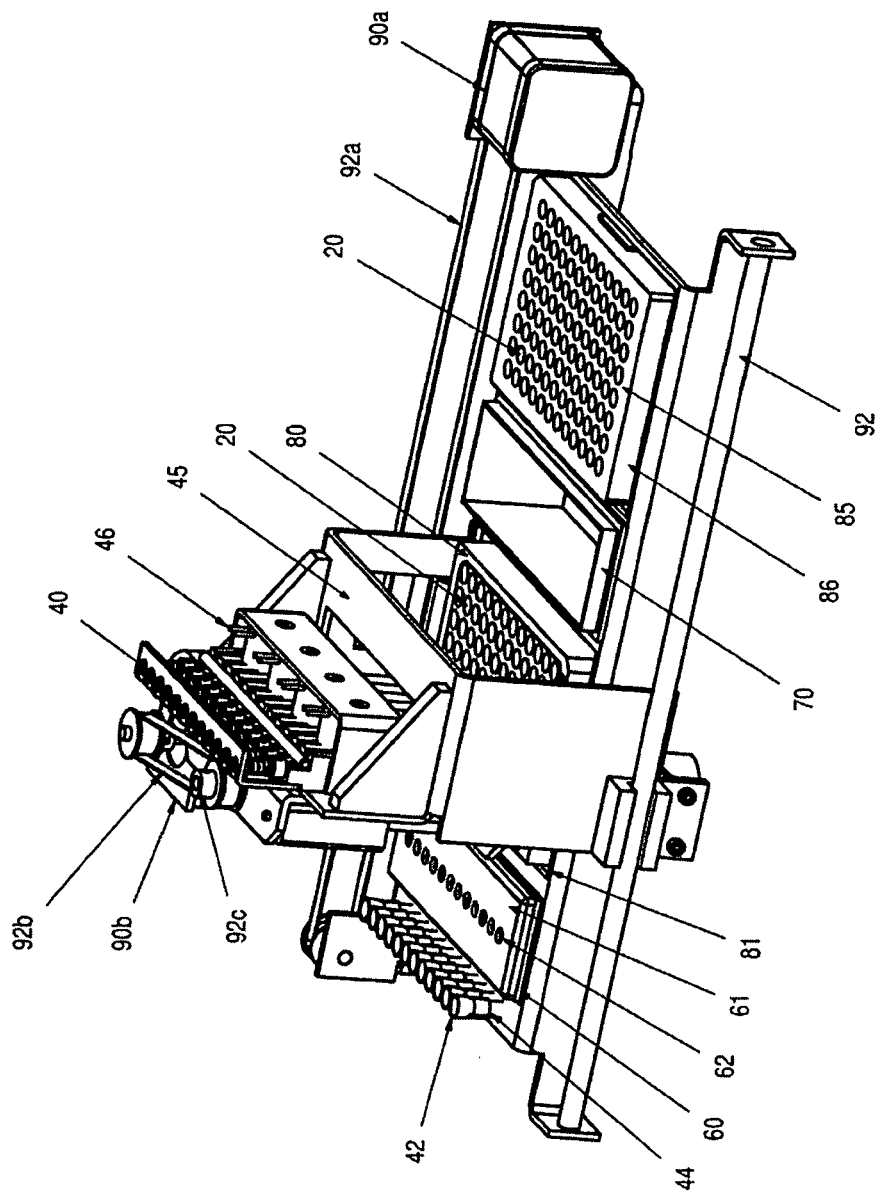

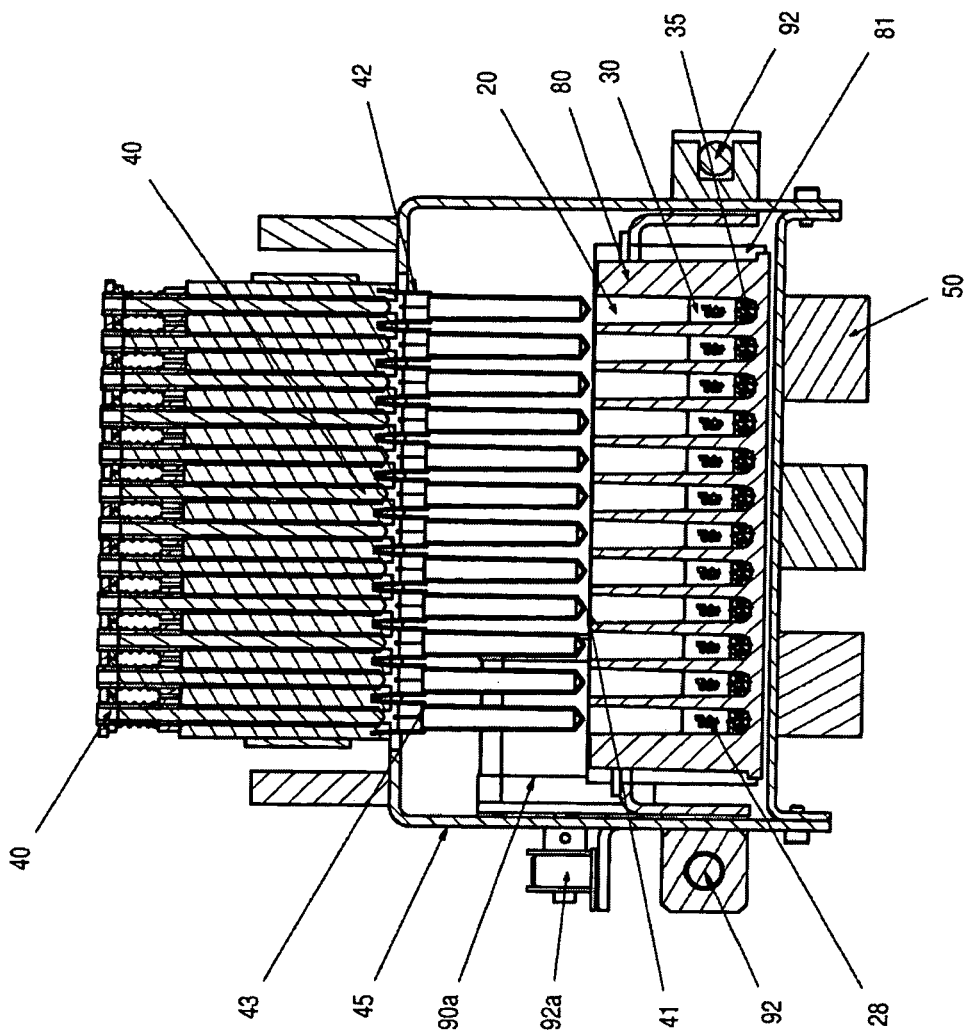

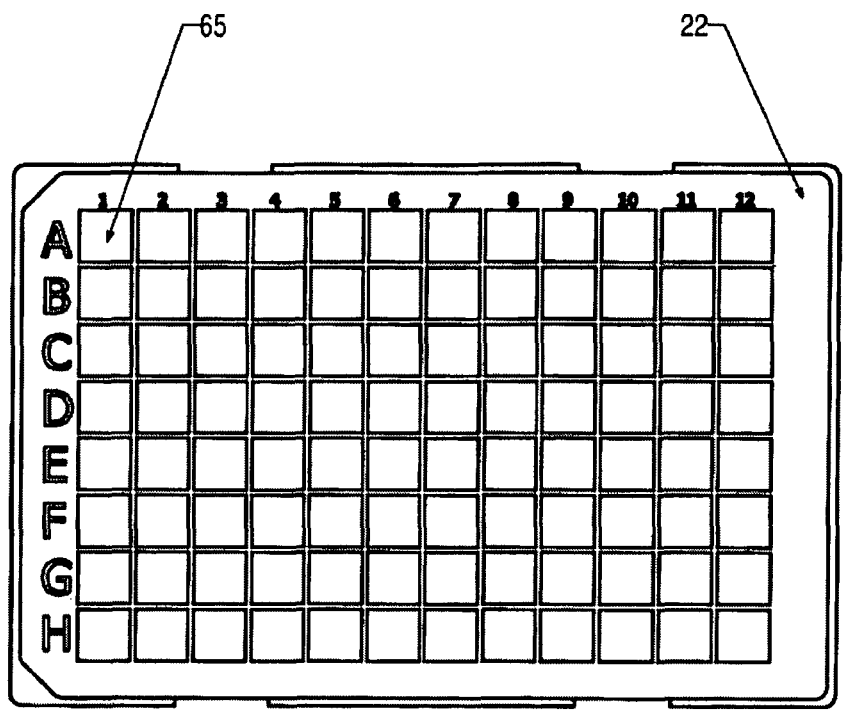
Fig 3.6

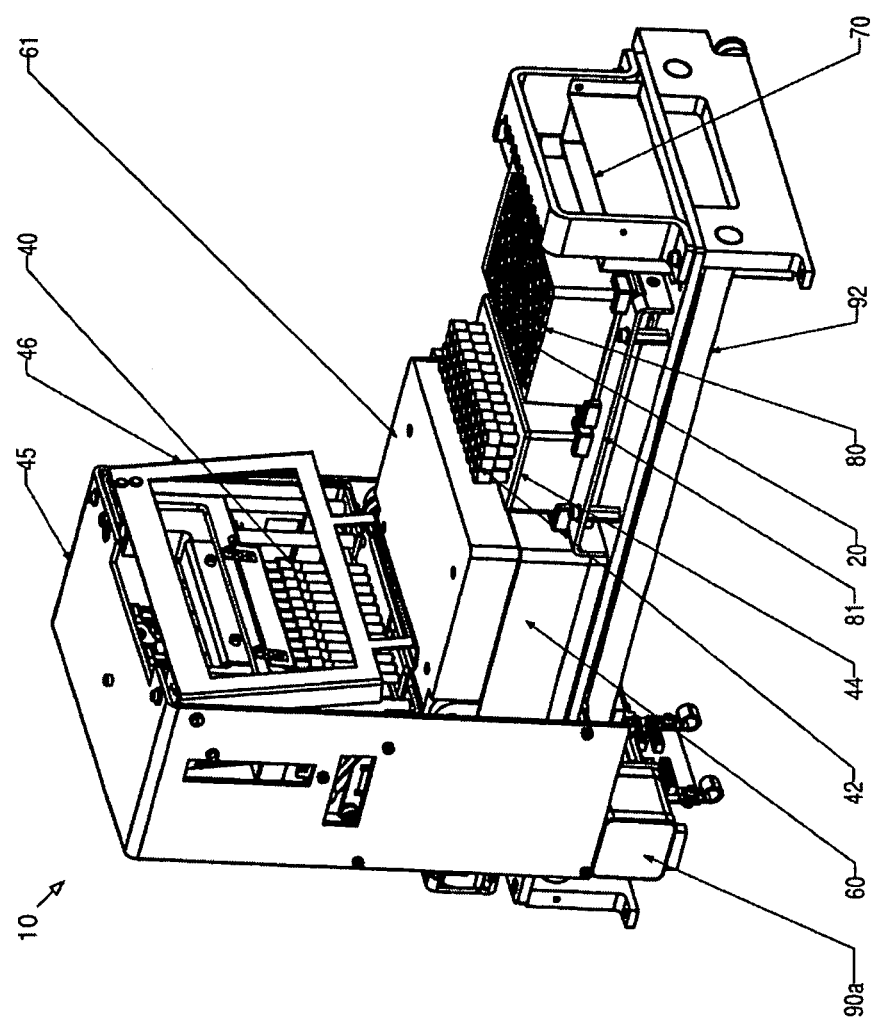

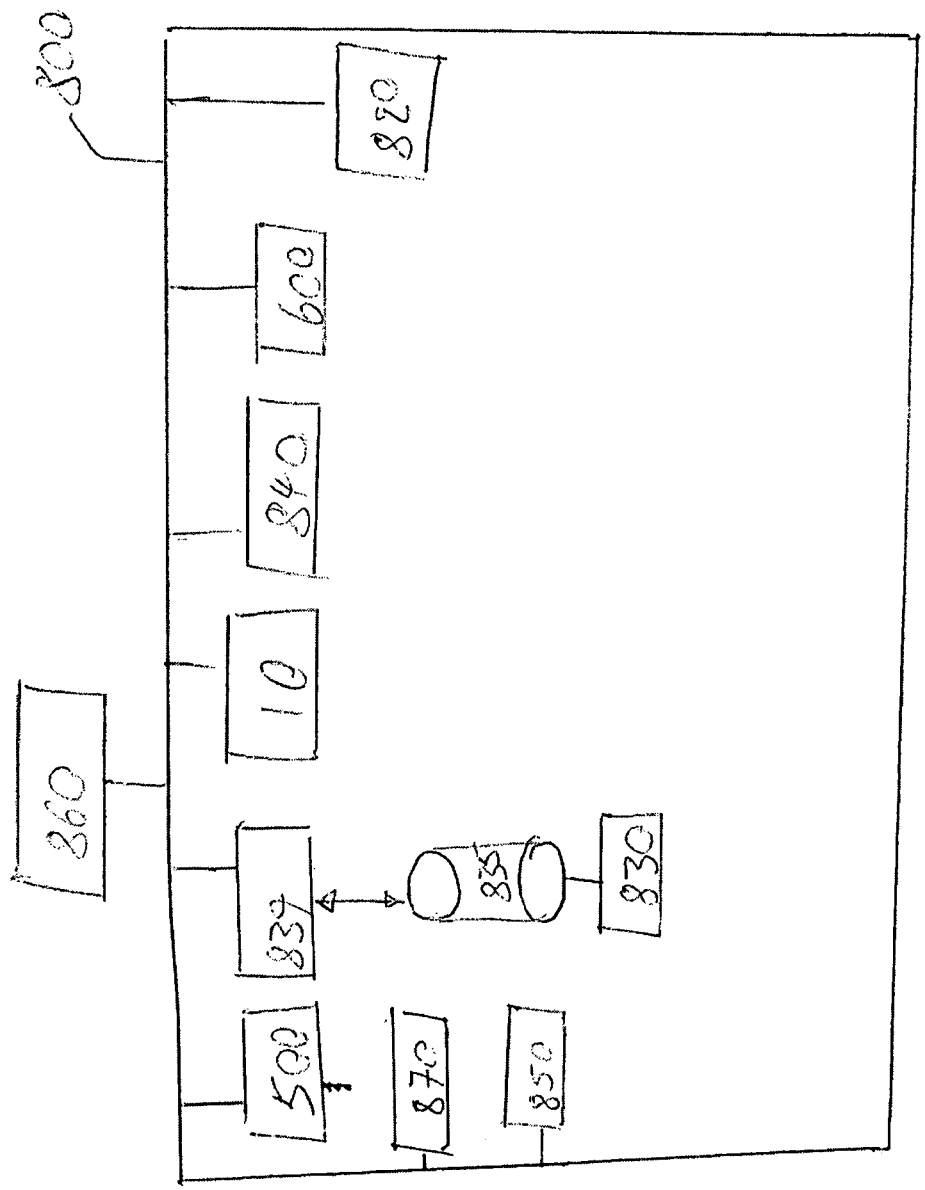

US 8,685,322 B2

APPARATUS AND METHOD FOR THE PURIFICATION OF BIOMOLECULES

This application claims the priority from German patent application DE 10 2007 054 033.9 to which reference is made and which in its entirety forms part of this disclosure.

FIELD OF INVENTION

The invention relates to an apparatus and a method for purifying biomolecules (e.g. DNA, RNA or proteins). The invention also relates to a system and a method for diagnostically purifying biomolecules.

DESCRIPTION OF RELATED ART AND BACKGROUND OF THE INVENTION

Apparatus and methods for the purifying of biomolecules via an adsorption to magnetizable particles are known in the art. The known methods are determined by the type of biomolecules and an interaction of the biomolecules with the magnetizable particles. These known methods of purifying are adapted for an automation of the methods for the purifying of biomolecules.

Among known suppliers of apparatus and methods for the purifying of biomolecules are: Chemagen, Qiagen, Thermo, Promega, Roche Diagnostics, Agowa, Dynal, Thermo Fisher, Analytik Jena and Tecan.

The known suppliers have partly protected their apparatus through their own patents (for example WO 03/044537, WO 2007/020294, U.S. Pat. No. 6,448,092 and WO 9609550).

Most of the known apparatus have in common that they are so-called magnet separators without a pipetting function (Thermo Kingfisher, Promega, Agowa). An operator pipettes solutions prior to an extraction process of the biomolecules by hand, or the operator uses prefilled plastic cavities for the extraction process of the biomolecules. In an apparatus supplied by Chemagen the cavities are also pre-filled, but an eluate still needs to be removed by pipetting manually. These approaches are sufficient for applications in research; however, they are not sufficient for diagnostics.

An apparatus offering a further solution is the Magnapure technology by Roche Diagnostics.

European patent application No. 0 644 425 by Hoffmann-La Roche discloses an analysis apparatus with a device for separating magnetic microparticles from a suspension. The apparatus disclosed in the Hoffmann-La Roche application comprises two permanent magnets between which a reaction cavity containing the suspension is disposed. The permanent magnets are arranged diametrically opposite each other with respect to the reaction cavity. The polar axes of the permanent magnets and the longitudinal axis of the reaction cavity form an acute angle. With this arrangement of the polar axes the magnetic stray field can be used for the separation of the magnetic microparticles, thereby accelerating the separation of the magnetic microparticles.

U.S. Pat. No. 6,596,162 (Thermo Labsystems Oy) and U.S. Pat. No. 6,040,192 (Labsystems Oy) disclose an apparatus for separating magnetic particles from a reaction cavity with a removable permanent magnet.

A use of the permanent magnets and suspensions with magnetic particles is common to the known apparatus. The magnetic particles are collected from the suspension and adhere to the permanent magnet due to the magnetic force. The magnetizable particles are released again after removing the magnetic field.

U.S. Pat. No. 6,409,925 B1 (Bio-Magnetics Ltd.) discloses an apparatus for a collecting of magnetic particles as well as a transferring of the magnetic particles from a first cavity to a second cavity. For the collecting and the transferring of the magnetic particles teaches a mobile magnetic element in order to magnetize a tip. A magnetization of the tip occurs upon approaching the mobile magnetic element to the tip. The magnetized tip is adapted for the collecting and the transferring of the magnetic particles.

EP 1 726 963 A2 (Festo Corporation) discloses a system for transferring a sample material from a source cavity to a target cavity. A transfer unit comprises at least one pin tip with a central bore and a magnetic actuator element. The actuator element is moveable between a first and a second actuator position. The sample material in proximity of the pin tip is either collected or released by moving the actuator element. Furthermore a group of counter magnets is provided underneath the source cavity and/or the target cavity, in order to support the transferring of the sample material. The Festo application furthermore allows a common movement of the actuator element and the group of counter magnets in order to mix the sample material. Each of the pin tips is individually controllable; likewise, a movement of each of the counter magnets is individually controllable.

The above-mentioned solutions have a disadvantage of qualitative shortcomings in a production of an eluate. The majority of the above mentioned solutions do not fulfill requirements of in-vitro diagnostics.

The purifying of the biomolecules using the magnetizable particles leads to "residual particles" in the eluate according to the methods known in the art. The "residual particles" have to be removed at a great effort in a further process step, for example, by centrifugation, since the "residual particles" impair subsequent analytic processes.

So far the purifying of the biomolecules comprised numerous sources of errors. The numerous sources of errors typically lead to at least one of a contamination, falsely negative results or falsely positive results. The numerous sources of errors are due to the chain of process steps. The process steps comprise a lysis of the sample material, a selection of substances and reagents. The process steps yield the eluate.

Furthermore, there is a danger of confusion when combining substances within a kit used for the purifying of biomolecules. A kit consists of a defined combination of substances and reagents. The substances and the reagents comprise, for example, an elution buffer. A use of a wrong elution buffer would, for example, lead to the biomolecules no longer being separable from the biomolecules bound to the magnetizable particles using the elution buffer. Thus the biomolecules would erroneously no longer be detectable in the eluate. It is of interest to prevent this.

The present invention uses, for example, among kits of the substances for the purifying of nucleic acids which are available for example from Invitek (disclosed, for example, in: WO 01/70386, WO 2004/042058, DE 10253351, WO 00/34463, WO 99/32616, U.S. Pat. No. 6,037,465, DE 59610721, DE 4422044 and others). Specifically, the present invention uses magnetizable particles adapted to temporarily bind the biomolecules, thus rendering the biomolecules transportable.

The kits of the substances by Invitek require temperatures of up to 90° Celsius over a period of, for example, 20 minutes. The temperatures of up to 90° Celsius are required during the lysis of the sample material. Sometimes large sample volumes have to be processed. The large sample volumes are not provided by conventional incubation systems. The conventional incubation systems may further not withstand the temperatures of up to 90° Celsius during the lysis of the sample material. Therefore special types of incubators are required.

Furthermore a required sample volume varies with a desired yield of biomolecules. The required sample volume depends very strongly on the field of application. Consequently, in practice problems have frequently occurred with an apparatus that can only cover a predetermined, narrow volume range in an automated processing.

SUMMARY OF THE INVENTION

An apparatus for purifying biomolecules comprises a plurality of cavities for accommodating solutions with magnetizable particles. Furthermore the apparatus comprises at least one magnetizable pin that is arranged such that the at least one magnetizable pin is insertable in at least one of the cavities, and at least one counter magnet is arranged in at least one bottom area of the cavities.

Lysis cavities and a work plate may be used as the cavities within the apparatus. Optionally also a yield plate may serve as the cavities. The yield plate may be arranged outside the apparatus forming a component of a system for diagnostically purifying biomolecules.

The apparatus and the method according to the invention provide the purifying of the biomolecules. The purifying of the biomolecules comprises a lysis and an extraction of the biomolecules (e.g. DNA, RNA or proteins) yielding the final eluate. The final eluate contains the biomolecules in suspension. The biomolecules in the suspension correspond to the requirements of clinical in-vitro diagnostics (IVD). The sample material can be of various types. Application of the invention reaches from the field of research to the field of clinical IVD. The purifying occurs by an adsorption of the biomolecules to magnetizable particles. A complete execution of the method according to the invention is rendered possible within the apparatus according to the present invention. The apparatus executes a complete method for the lysis, the extraction and the purifying of the biomolecules without any intervention by a laboratory staff. The sample material (e.g. blood, patient tissue, blood plasma, blood serum) bears a machine-readable identification. The sample material is placed into the apparatus at a start of the method. Selectively, the sample material is linked to an unambiguously identified processing job.

The apparatus controls an addition of the substances and the reagents as well as required process parameters for controlling the method. The control of the apparatus is selectively based on the unambiguously identified processing job or on a program. The substances and the reagents as well as the required process parameters for controlling the method are derived from the machine-readable identification of the sample material. The method is documented and takes place without possibility of interference by the laboratory staff. Therefore there is no danger of confusion, a strongly reduced danger of infection and no danger of contamination or cross-contamination.

The present invention is adapted to use a plurality of cavities for accommodating mixtures of the sample material and reagents. The invention discloses a method for enhancing a minimum and a maximum sample volume. The invention further discloses an enhancement of a processable amount of the biomolecules. The various aspects of enhancement are referred to as upscaling.

Moreover, the invention discloses a closable incubation unit adapted to generate a homogeneous temperature within the cavities. The homogeneous temperature within the cavities yields a homogeneous temperature in the mixture of the sample material and the reagents within the incubation unit. The homogeneous temperature within the sample material and the reagents is reachable within a few minutes. The incubation unit is adapted to stabilize the homogeneous temperature with great precision without any liquid evaporating.

The invention furthermore discloses a method for purifying biomolecules within the mixture of the sample material and the reagents using magnet particles or magnetizable particles. The term purifying also includes the lysis of the biomolecules. The method comprises a mixing of the biomolecules with a binding buffer and the magnetizable particles, thereby forming a particle-biomolecule complex, wherein the biomolecules are bound to the magnetizable particles by the binding buffer.

The method furthermore comprises a switching on or an inserting of a magnetizable pin. Moreover the method comprises a transporting of the particle-biomolecule complex to a first cavity with a first solution. In addition the method comprises a switching off of the magnetizable pin, an optional switching on of a counter magnet and a mixing of the particle-biomolecule complex with the first solution.

The method and the apparatus for the purifying of the biomolecules, use one or two groups of magnets, a plurality of magnetizable pins and at least one counter magnet. Thereby it is possible to substantially reduce the number of magnetizable "residual particles" present in the eluate. The group of counter magnets allows a retention of the "residual particles" present in the eluate in the cavity. Thereby a purity of the eluate is improved and consequently a functionality of subsequent analyses is improved.

The invention furthermore discloses a system for diagnostically purifying biomolecules. The term "diagnostically purifying" includes the lysis and the extraction of the biomolecules. The system according to the invention comprises the apparatus for purifying the biomolecules according to the invention. The system furthermore comprises a control unit for controlling the apparatus. The system yields an eluate with diagnostically purified biomolecules from the sample material. Moreover, the system comprises a detection unit adapted to detect a code. The detection unit furthermore transfers the code to a yield cavity.

Furthermore the invention discloses a method for the diagnostically purifying of biomolecules comprising an execution of the method for purifying the biomolecules according to the invention to yield an eluate with the diagnostically purified biomolecules from the sample material under the effect of magnetizable particles.

FIGURES

Figure 2:
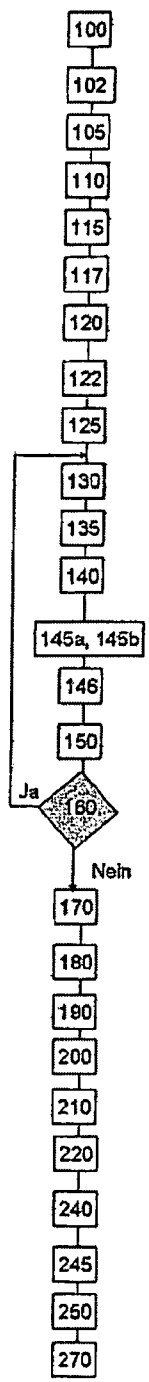
Figure 3A:
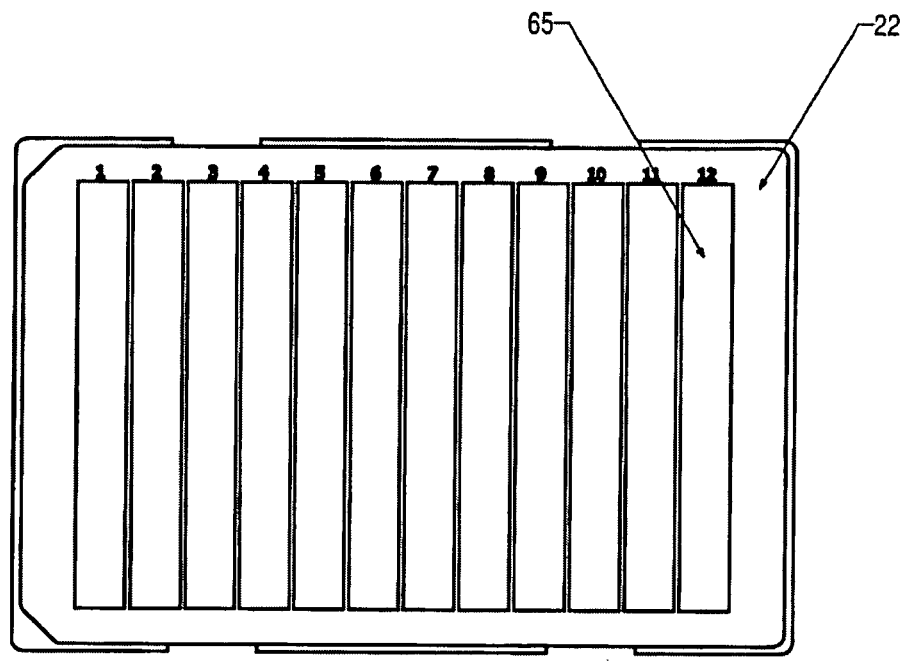
Figure 3C:
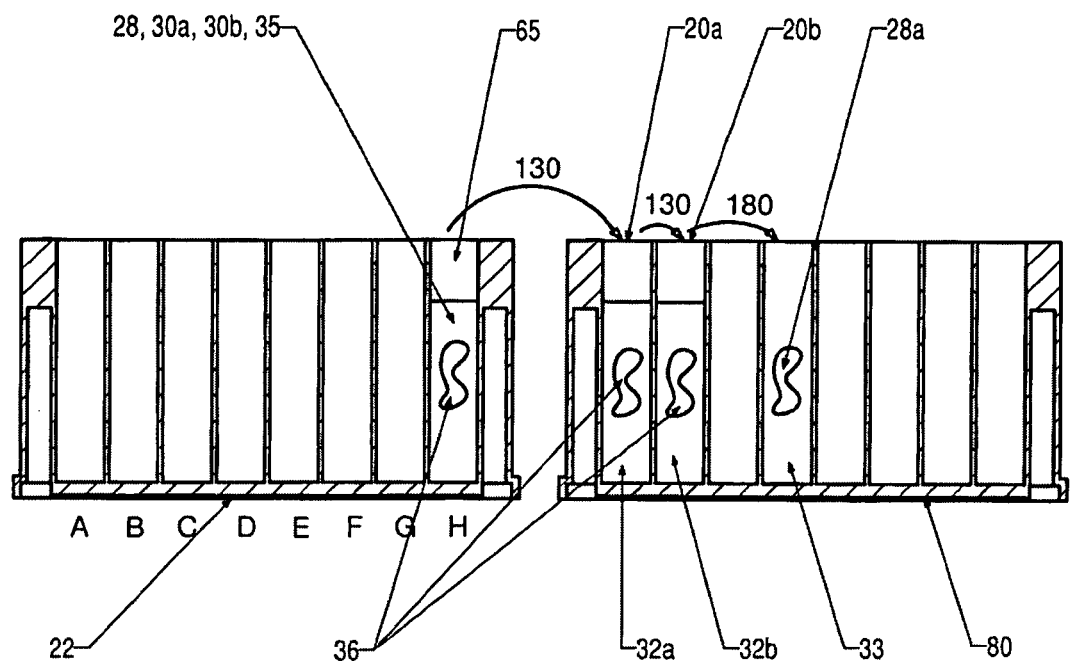
Figure 3D:
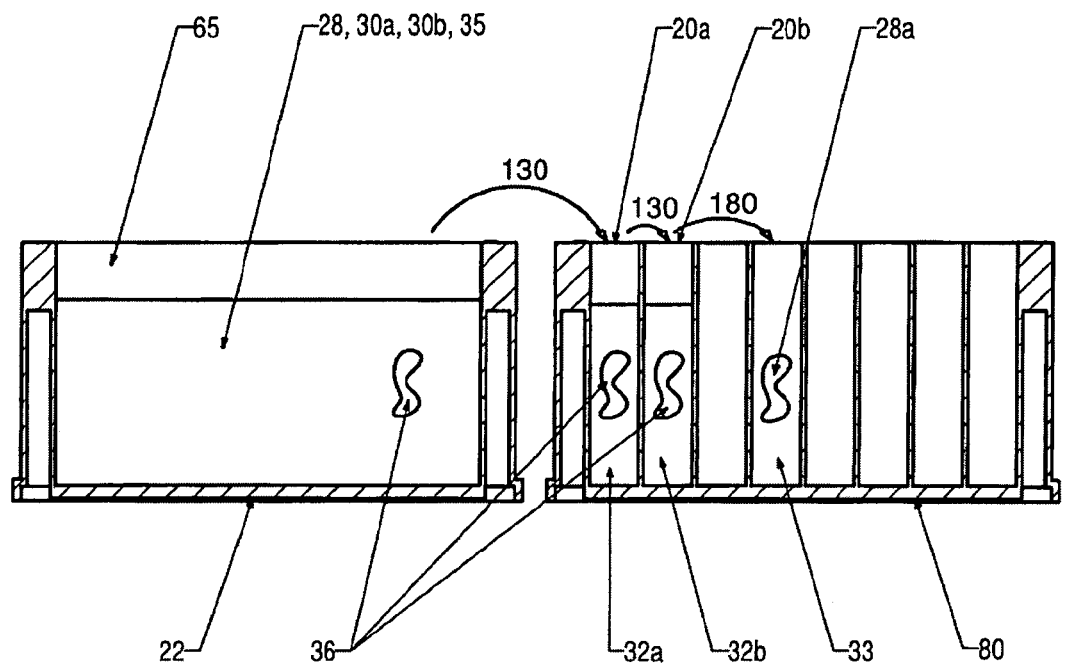
Figure 3E:
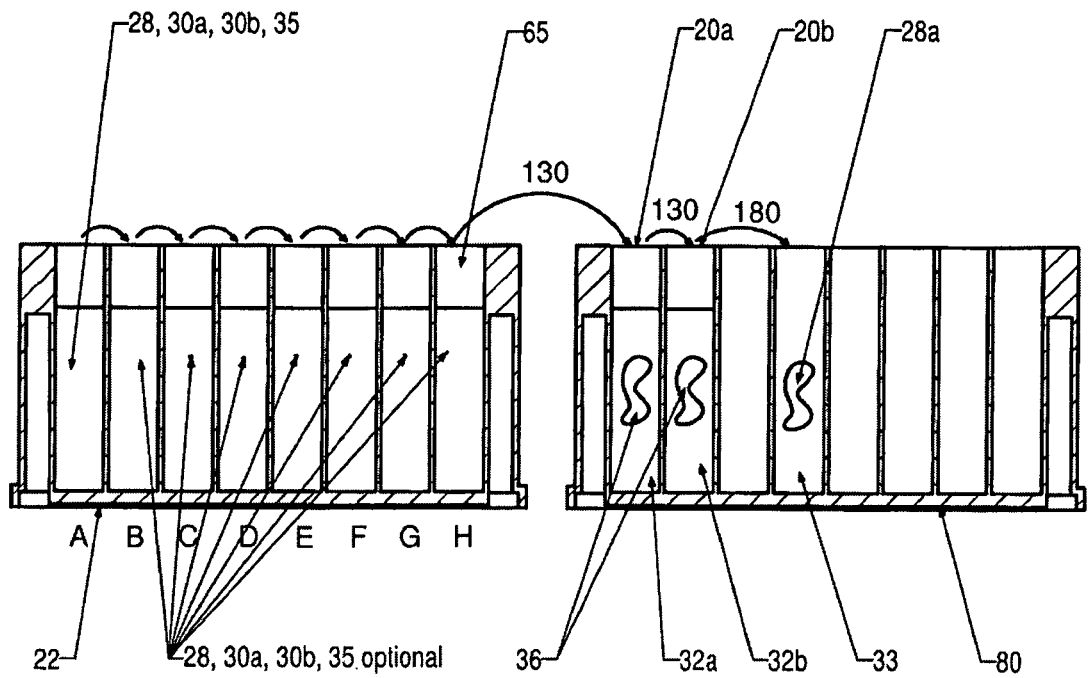
Figure 3F:
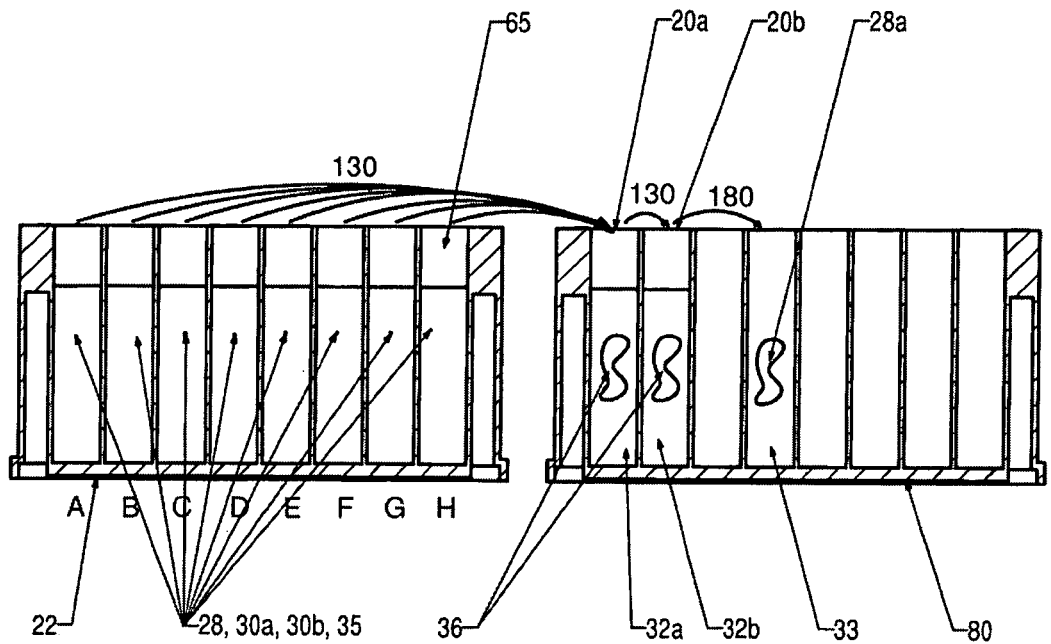
Figure 46:
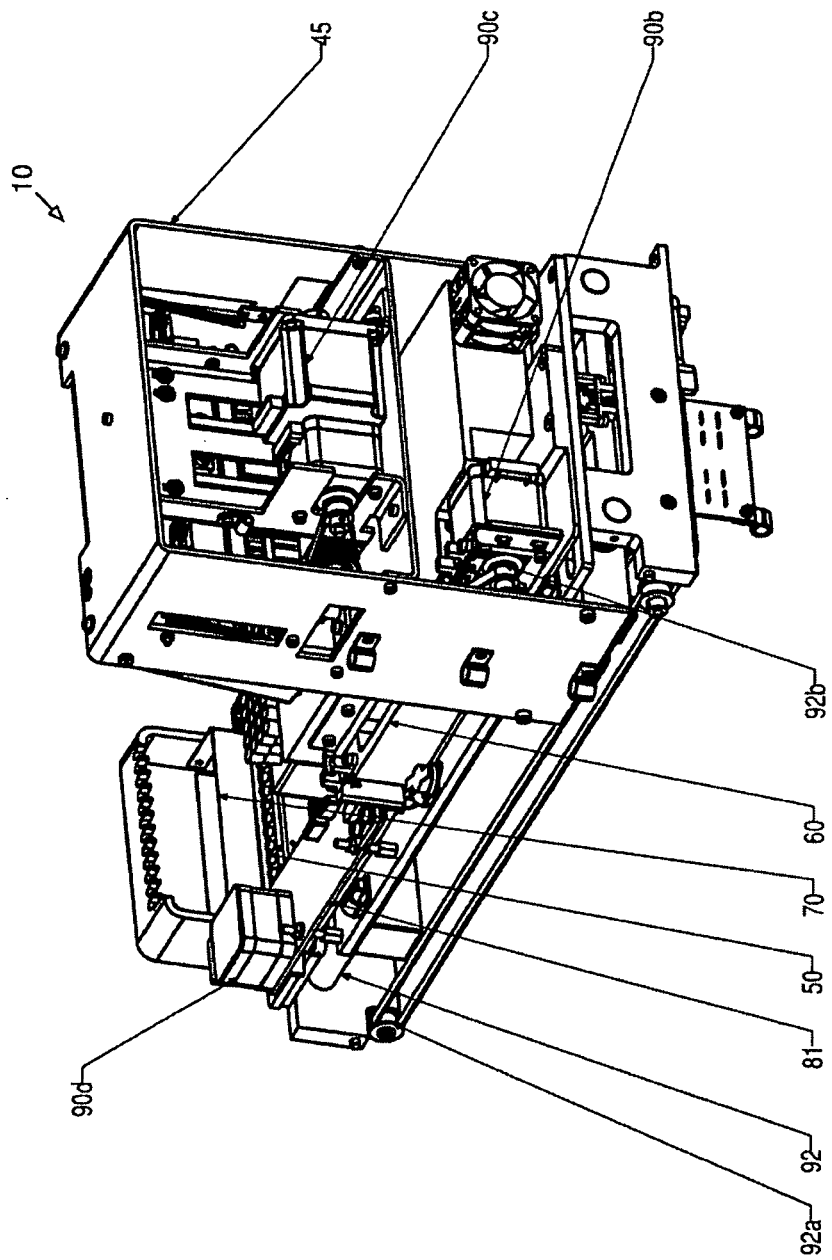
Figure 4C:
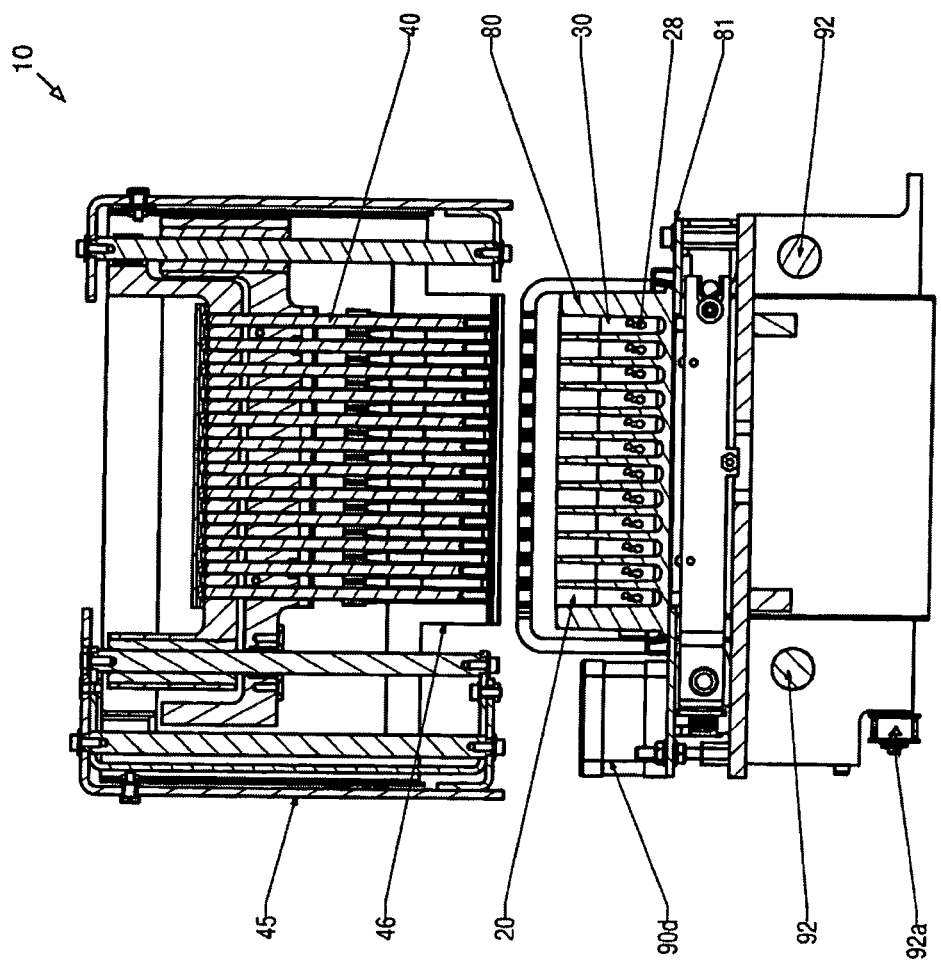
Figure 40D:
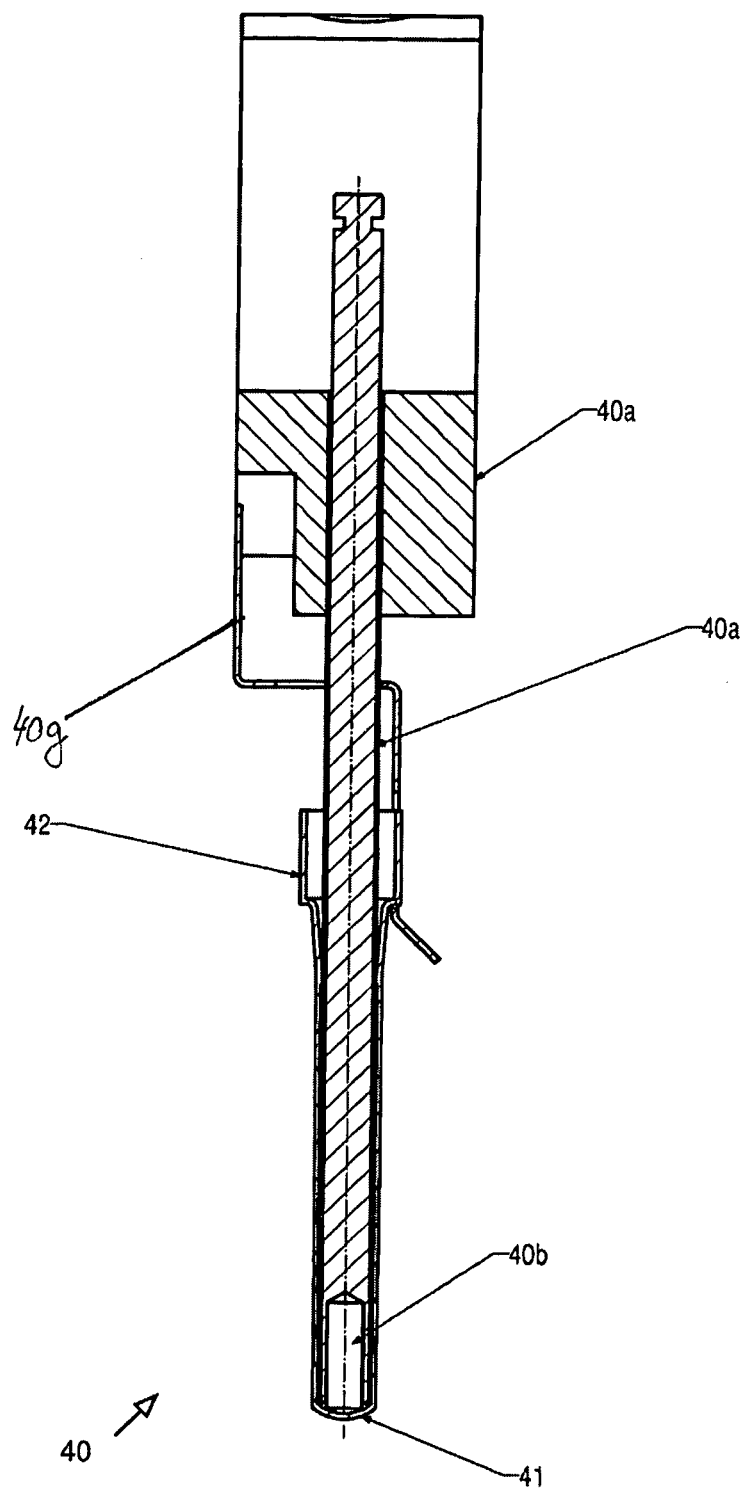
Figure 5A:
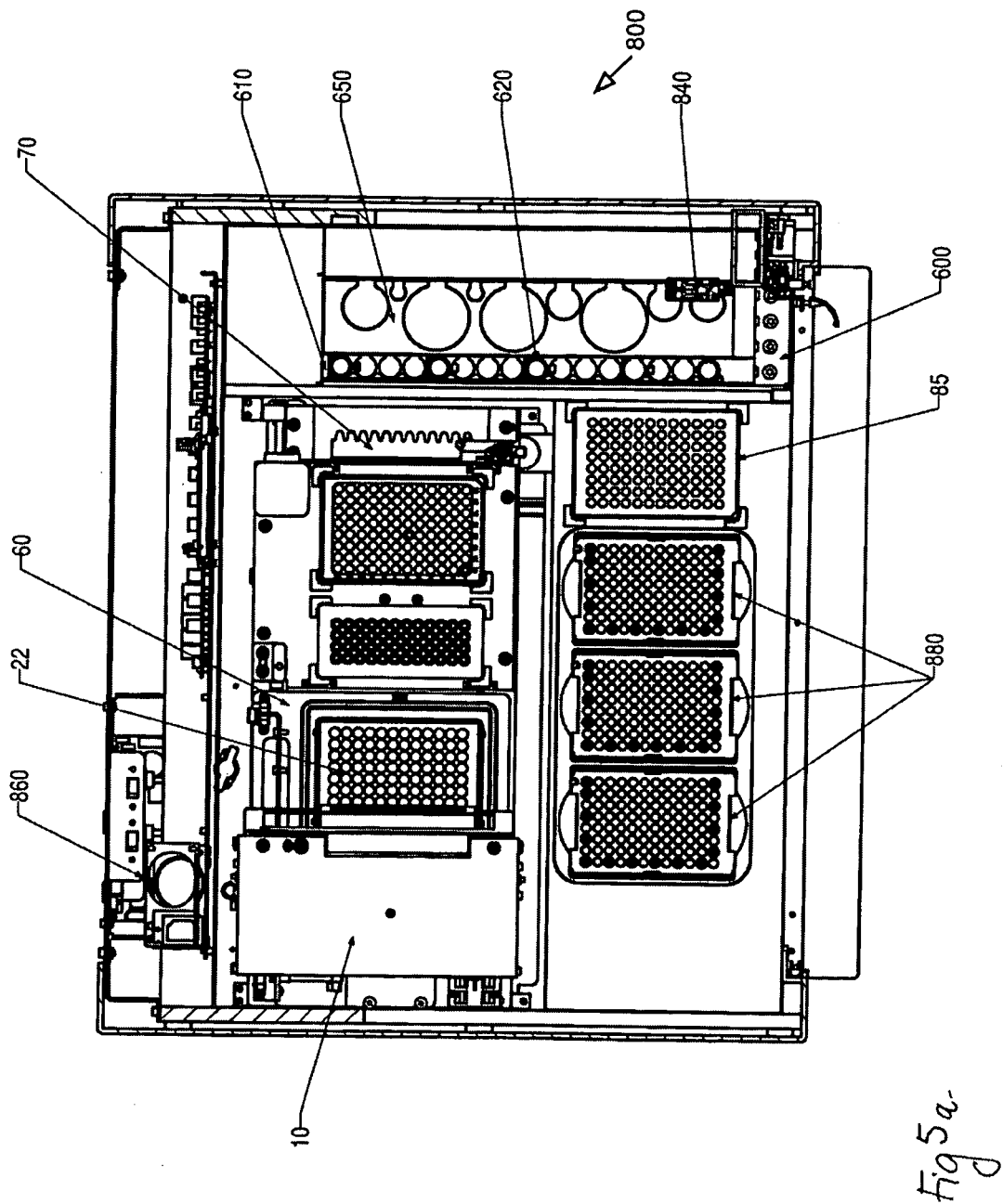
Figure 5B:
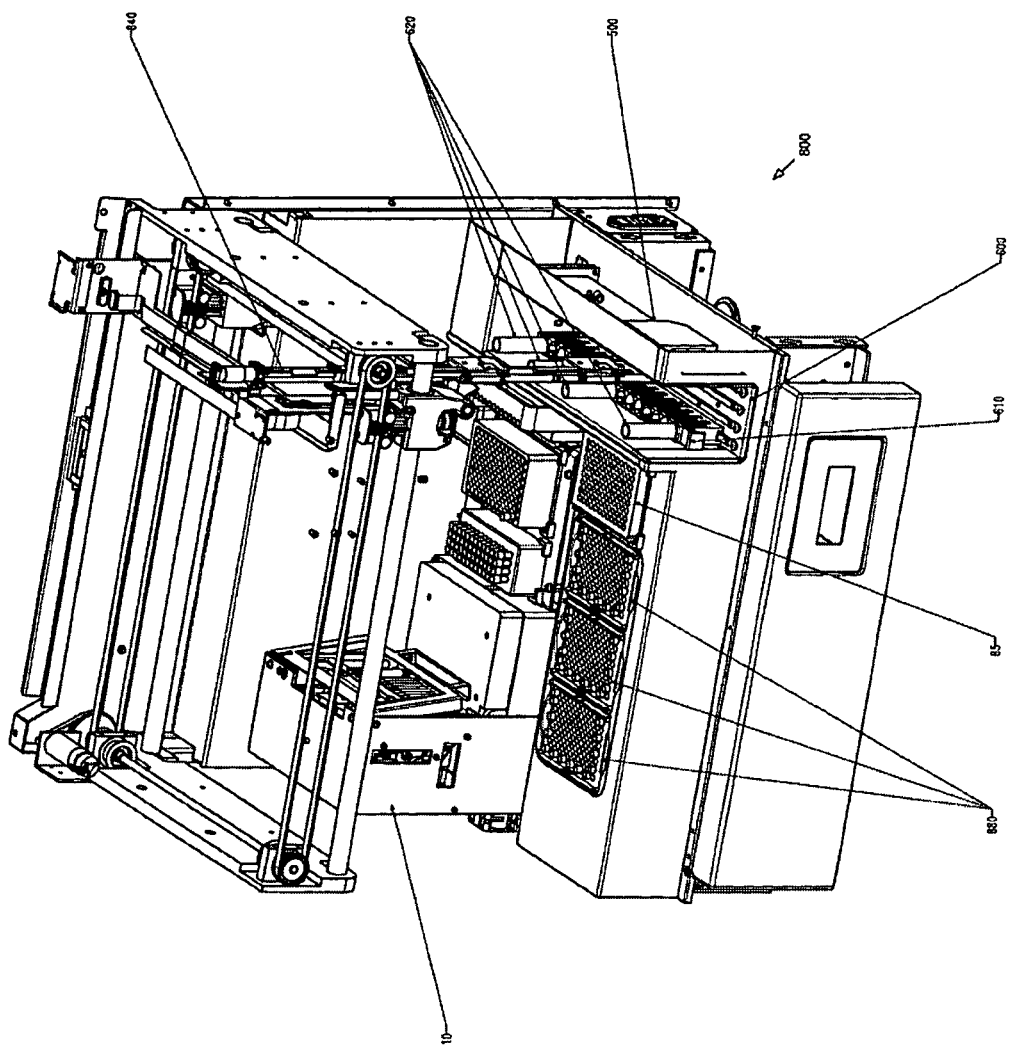
Figure 6A:
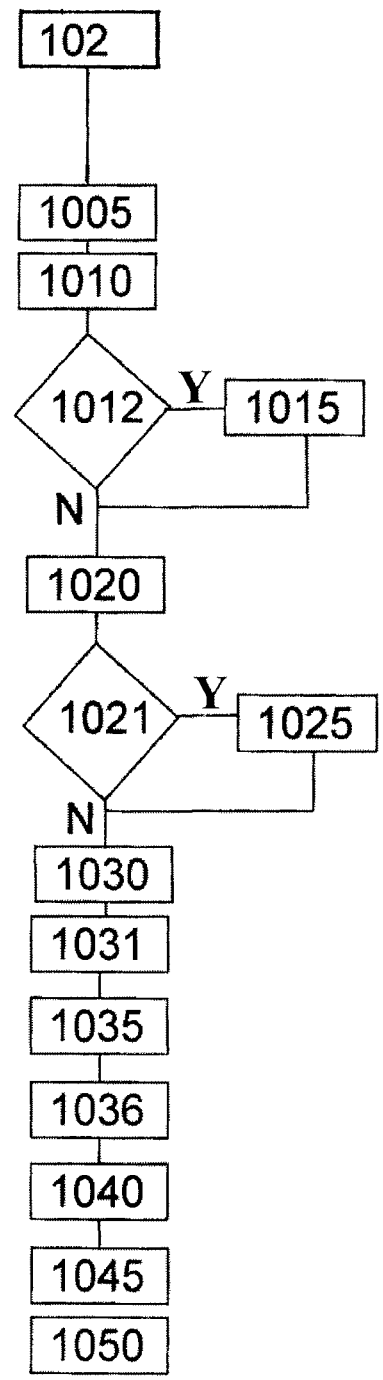
Figure 6B:
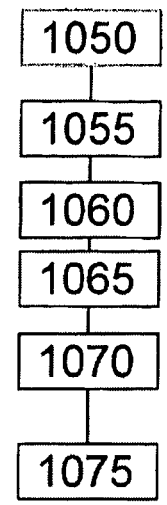

FIG. 1a shows a perspective view from above of the apparatus according to the invention FIG. 1b shows a perspective view from below of the apparatus according to the invention FIG. 1c shows a cross section of the apparatus according to the invention FIG. 2 shows the method according to the invention as a flow chart FIG. 3a shows an example of a plate with large incubator cavities in 12 rows from above FIG. 3b shows an example of a plate with 8 times 12 incubator cavities from above FIG. 3c shows a method without upscaling FIG. 3d shows a method with an upscaling from a large cavity FIG. 3e shows a method with an upscaling from standard cavities FIG. 3*f* shows a further method with an upscaling from standard cavities FIG. 4*a* shows a perspective lateral view of an alternative aspect of the apparatus FIG. 4*b* shows a perspective view from behind of the alternative aspect of the apparatus FIG. 4*c* shows a cross section of the alternative aspect of the apparatus FIG. 4*d* shows a magnetizable pin according to the invention FIG. 5*a* shows a top view of a system according to the invention FIG. 5*b* shows a perspective view of the system according to the invention FIG. 6*a* shows a method for diagnostically purifying biomolecules FIG. 6*b* shows a section of the method for diagnostically purifying the biomolecules FIG. 7 shows a block diagram of the system according to the invention

DETAILED DESCRIPTION OF THE INVENTION

The invention will now be described on the basis of the drawings. It will be understood that the embodiments and aspects of the invention described herein are only examples and do not limit the protective scope of the claims in any way. The invention is defined by the claims and their equivalents. It will be also understood that features of one aspect can be combined with features of a different aspect.

FIGS. 1*a*-1*c* show a perspective view of an apparatus 10 for purifying biomolecules 28 according to one aspect of the invention. The apparatus 10 comprises on one level a row of fasteners or a rack 44 for disposables, for example, plastic covers 42, an incubation unit 60, a work-area retainer 81 for a work plate 80, an accommodation cavity 70 for used disposables, as well as a yield-area retainer 86 for a yield cavity 85. A first drive motor 90*a* and a first band 92*a* are mounted on the one level. The work-area retainer 81 and the yield-area retainer 86 each have a plurality of cavities 20.

The apparatus 10 has a frame 45 with magnetizable pins 40 with electric connections 46. The frame 45 comprises a second drive motor 90*b*, a second band 92*b* and a spindle 92*c*.

Counter magnets 50 with electric connections 51 are disposed below the one level underneath the work-area retainer 81 (see FIG. 1*b*). The racks 44 for the disposables are provided next to the incubation unit 60.

The disposables are preferably the plastic covers 42. The plastic covers 42 are made of polypropylene or any other suitable material. An example of the plastic covers 42 described within the framework of this description is approx. 50.5 mm long and has a diameter of approximately 5.5 mm. The diameter of the plastic covers 42 widens to approx 8.5 mm toward the upper end of the plastic cover 42. A wall thickness of the plastic covers 42 is approximately 0.5 mm. Dimensions of the plastic covers 42 are chosen such that the plastic covers 42 fit ends 41 of the magnetizable pins 40 well (see FIG. 1*c*).

Of course other dimensions of the plastic covers 42 are possible, as long as the plastic covers 42 fit the ends 41 of the magnetizable pins 40 well and can still dip into the cavities 20 comfortably, without making liquids in the cavities 20 flow over.

For example the plastic covers 42 are caught on a bulge 43 of the magnetizable pins 40 (see FIG. 1*c*). The plastic covers 42 are disposed in the rack 44 for the disposables. The rack 44 for the disposables is adapted to accommodate the plastic covers 42 and is optionally filled by an automatic feeding system (not shown in FIGS. 1*a*, 1*b* and 1*c*).

The incubation unit 60 can accommodate at least one lysis cavity 22 (not shown) in a sample area. A sample material containing biomolecules 28 is placed in the lysis cavity 22. A filling of the lysis cavity 22 preferably takes place using a suitable pipetting system 840 in a fully automated or semi-automated process. The suitable pipetting system 840 is not shown in FIG. 1*a* to 1*c* and will be explained below in connection with a system 800 according to the present invention (see FIG. 5*a*).

Optionally the incubation unit 60 can be closed by a lid 61, as visible in FIG. 4*a*, or by a lid 61 with openings 62, as visible in FIG. 1*a*. Into the openings 62 the suitable pipetting system 840 can be lowered (see FIG. 5*b*). The incubation unit 60 allows a heating of the sample area to temperatures above a surrounding temperature. Preferably the openings 62 of the lid 61 are designed such that the openings 62 can be closed by lowering the magnetizable pins 40. Lowering the magnetizable pins 40 into the openings 62 facilitates achieving a target temperature within the lysis cavity 22 inside the incubation unit 60. Additionally moving the magnetizable pins 40 up and down in the lysis cavity 22 effects a mechanical mixing of the sample material comprising the biomolecules 28, at least one lysis buffer 30*a* and the magnetizable particles 35, in order to form a solution 30. The lysis buffer 30*a* and the magnetizable particles 35 were filled into the lysis cavity 22 beforehand by the suitable pipetting system 840 (shown on the right in FIG. 5*b*).

The optional lid 61, 62 of the incubation unit 60 may be removed after a selectable time interval to facilitate a cooling of the solution 30. Additionally or alternatively the cooling can be supported by a heat-dissipating device, e.g. a ventilator.

The work plate 80 can be implemented as a deep-well plate and can contain a first plurality of the cavities 20. For a conventional deep-well plate, each cavity 20 can hold a volume of approx. 2 ml. The volume of 2 ml is a suitable volume to accommodate, for example, blood samples and to purify the biomolecules 28, e.g. DNA or RNA material. The volume of 2 ml allows integrating the apparatus 10 in a method for purifying the biomolecules 28. The method may be executed in a fully automated way.

The yield cavity 85 can be implemented as a microtiter plate for accommodating purified biomolecules 28 in the solutions 30. Alternatively the yield cavity 85 can also be implemented by one or several lines of individual sample tubes accommodating the purified biomolecules 28.

A rake can be provided to facilitate a slipping off of the disposables above the accommodation cavity 70 for the used disposables; in particular the used plastic covers 42.

According to a further aspect of the present invention it may be of interest to arrange the accommodation cavity 70 for the used disposables between the work plate 80 and the yield cavity 85. It is thus ensured that the used disposables are not moved above the yield cavity 85; thereby further reducing unintentional contamination of the purified biomolecules 28.

The frame 45 is moved along one side of the apparatus 10, so that the frame 45 can sweep the rack 44 for the plastic covers 42, the incubation unit 60, the work plate 80, the yield cavity 85 and the accommodation cavity 70 for the used plastic covers 42. In the aspect of the apparatus 10 shown in FIG. 1*a*-1*c* the frame 45 is moved along the longitudinal side of the apparatus 10.

The frame 45 is moved by the first drive motor 90*a*. Preferably the frame 45 is implemented as a sliding carriage on two longitudinal rails 92 and the thrust of the first drive motor 90a is transferred to the carriage slide via the first band 92a, so that the frame 45 can be moved along the longitudinal axis of the apparatus 10. The first drive motor 90a can be controlled by suitable software.

The magnetizable pins 40 can be implemented as permanent magnets. Alternatively it is possible to implement the magnetizable pins 40 as electromagnets. FIG. 1a shows the electric connections 46 for controlling the magnetizable pins 40 implemented as the electromagnets.

The magnetizable pins 40 can be moved on the frame 45 in the z direction by the second drive motor 90b. In the embodiment of the apparatus 10 shown in FIGS. 1a-1c a movement of the second drive motor 90b is transferred to the spindle 92c via the second band 92b, so that the z position of the magnetizable pins 40 can be varied. The movement of the second drive motor 90b can also be controlled by the suitable software.

Dipping the magnetizable pin 40 into the solution 30 within the cavity 20 generates a magnetic field to which the solution 30 is subjected for the magnetizable pin 40 implemented as the permanent magnet. A current flow of suitable amplitude and direction has to be circuit-switched through the electromagnet in order to switch the magnetizable pin 40 to either a magnetic or a non-magnetic state. The current flow is required in addition to lowering the magnetizable pin 40 with the magnetizable pin 40 implemented as the electromagnet. Further a moving up and down of the magnetizable pin 40 in the z direction serves for mixing the solution 30 and/or to improve a collecting of the magnetizable particles 35 within the cavity 20.

In the aspect with permanent magnets instead of electromagnets a removal of the magnetizable pin 40 from the solution 30, corresponds to a switching off of the magnetizable pin 40. The removal of the magnetizable pins 40 from the solution 30 may also referred to as a switching off of the magnetic field of the magnetizable pins 40. Outside the solution 30 the magnetizable pin 40 does not exert a magnetic field on the solution 30 within the cavity 20.

In the aspect of FIGS. 1a-1c counter magnets 50 are arranged below the work plate 80, near the bottom area of the cavities 20 within the work plate 80. The counter magnets 50 are best seen in FIGS. 1b and 1c. A group of counter magnets 50 comprises at least one counter magnet 50. The counter magnets 50 can be implemented as an arrangement of permanent magnets, so that one of the counter magnets 50 corresponds respectively to one cavity 20 within the work plate 80. The position of the counter magnets 50 can be changed relative to the cavities 20 of the work plate 80. It is possible to approach the cavities 20 with the arrangement of the permanent magnets so that the cavity 20 is penetrated by the magnetic field of the counter magnets 50 in a bottom area.

In a second position of the arrangement of the permanent magnets the counter magnets 50 are sufficiently spaced apart from the cavities 20, and the magnetic field of the counter magnets 50 essentially vanishes in the bottom area of the cavities 20. The magnetic field of the counter magnets 50 thus can be switched by a suitable position of the counter magnets 50 implemented as the arrangement of the permanent magnets. As for the aspect according to FIG. 1b the counter magnets 50 are allocated to the cavities 20. In FIG. 5b one of the counter magnets 50 is allocated to several ones of the cavities 20. Likewise it would be possible to allocate to each of the cavities 20 an individual one of the counter magnets 50.

Alternatively or additionally it is possible to provide only one row of the counter magnets 50, so that one of the counter magnets 50 corresponds to a number of columns within the work plate 80. The apparatus 10 comprises a device for moving the row of counter magnets 50 with the movement of the frame 45 and thereby a movement of the magnetizable pins 40. It would be possible to couple the movement of the row of counter magnets 50 to the movement of the first band 92a. If the row of counter magnets 50 is embodied as the permanent magnets, it is necessary that the row of counter magnets 50 is mobile along the z direction in order to switch the magnetic field in the bottom area of the cavities 20 of the work plate 80 either on or off.

Moreover it is possible to implement the counter magnets 50 as a single counter magnet 50 that is moved from one cavity 20 to the next. The single counter magnet 50 moves along a grid in the x and y direction to cover all the cavities 20. However, for the apparatus 10 with a plurality of magnetizable pins 40, using the single counter magnet 50 is slower than using the two aspects of the counter magnets 50 mentioned above.

The counter magnets 50 can be implemented as the electromagnets for all the aspects of the counter magnets 50 described above. The electromagnets induce the magnetic field in the bottom area of the cavities 20 upon the current flow. The magnetic field of the counter magnets 50 vanishes substantially as soon as no current flows through the electromagnets any longer. Hysteresis effects within the electromagnets limit a speed of switching the counter magnets 50 when implemented as the electromagnets. The speed of switching is further limited by diffusion processes of the magnetizable particles 35 within the solutions 30. A polarity of the current flow is to be chosen such that the magnetizable particles 35 are subjected to a force in the direction of the bottom area of the cavity 20 when the magnetic field is switched on. It is consequently possible to switch the magnetic field of the counter magnets 50 on and off depending on the current flow with the apparatus 10 comprising the counter magnets 50 implemented as the electromagnets. It is of interest to have the software controlling the apparatus 10 to switch the counter magnets 50 on and off. The counter magnets 50 implemented as electromagnets are shown in FIG. 1b with the electric connections 50a.

In FIG. 1c furthermore the solutions 30 are shown within the cavities 20. The solutions 30 can still contain residual amounts of the magnetizable particles 35 even after the last stage of a production of the eluate. The counter magnets 50 support a movement of the magnetizable particles 35 toward the bottom area of the cavities 20. The counter magnets 50 generate a shift of the residual magnetizable particles 35 toward the bottom area of the cavities 20. The shift of the residual magnetizable particles 35 improves the eluate, such that the eluate is free from the magnetizable particles 35 in an upper layer of the cavity 20. The eluate is transferred from the upper layer out of the cavity 20 into the yield cavity 85 using the pipetting system 840.

FIG. 2 shows a method 100 for purifying the biomolecules 28 according to the invention. The apparatus 10 and the method 100 allow a complete execution of the method 100 within the apparatus 10.

In a step 102 the frame 45 with the magnetizable pins 40 is moved over the rack 44 for the plastic covers 42 and is lowered, so that one of the plastic covers 42 is slipped onto each one of the magnetizable pins 40.

A conventional sample cavity (not shown in FIGS. 1a and 1b) contains the sample material to be lysed. The conventional sample cavity plus a buffer are placed in a step 105 in the apparatus 10. The conventional sample cavity can, for example, be a tube with blood serum. The conventional sample cavity in addition bears an unambiguous identification. The unambiguous identification, for example, a barcode, rules out unintentional confusion of the sample material. The method 100 has to enable the identification of the sample materials, without any danger of confusion, if the method 100 is to be used in diagnosis of the biomolecules 28. The apparatus 10 and the method 100 according to the present invention rule out any confusion of the sample material. Barcode scanners can document the execution of the method 100 within the apparatus 10.

In a step 110 an aliquot of the sample material is placed into the lysis cavity 22 using the suitable pipetting system 840 (shown in FIG. 5b). In addition the suitable pipetting system 840 pipettes 115 the lysis buffer 30a into the lysis cavity 22.

All of the following examples of buffers are used in a purifying for DNA from whole blood; other sample materials partly require other buffer systems. An example for the lysis buffer is Lysis Buffer A for blood samples, such as used in a variety of kits by Invitek. This buffer is based on the patent DE 19856064 C2.

In step 117 a lysis procedure takes place. The lysis procedure may take place at elevated temperatures provided by the incubation unit 60 accommodating the lysis cavity 22. A mechanical mixing of the solution 30 in the lysis cavity 22 is possible by moving the magnetizable pins 40 up and down in the lysis cavity 22 during the lysis procedure 117. The lysis procedure 117 takes between 10-30 minutes, depending on the biomolecules 28. The mixing during the lysis procedure 117 can either take place by a cyclical opening of the lid 61 of the incubation unit 60 or with the lid 61, 62 removed.

During the lysis procedure 117 the apparatus 10 prepares the cavities 20 arranged in the accommodation area 81 of the work plate 80 with the washing buffers 32a and 32b and the elution buffers 33 using the suitable pipetting system 840, preferably first a first washing buffer 32a, then second a second washing buffer 32b. Without limitation more than two washing buffers 32a, 32b are possible. Furthermore at least one elution buffer 33 is pipetted into the cavities 20. Examples for washing buffers are Wash Buffer I and Wash Buffer II, an example for the elution buffers is Elution Buffer D. These buffers are based on the patent DE 19856064 C2.

Subsequently follows an addition 120 of a binding buffer 30b and the magnetizable particles 35 to the lysis cavity 22. Examples of the binding buffers are Binding Buffer B6 or Binding Buffer. These buffers are based on the patent DE 19856064 C2.

The biomolecules 28, the binding buffer 30b and the magnetizable particles 35 are mixed 122 within the lysis cavity 22 by moving the magnetizable pins 40 of the apparatus 10 up and down. Optionally the pipetting system 840 can be used for mixing. The mixing by the pipetting system 840 comprises absorbing and dispensing the solution.

Subsequently the magnetizable pins 40 are switched to magnetic 125, for example, by switching on the current flow and the magnetizable particles 35 are collected.

The biomolecules 28, e.g. nucleic acids 28a, have now attached themselves to the magnetizable particles 35 in order to form a particle-biomolecule complex 36. The magnetizable particles 35 with the bound nucleic acid 28a are transported 130 by the apparatus 10 through the washing buffers 32a, 32b; according to the following principle for each washing buffer 32a or 32b etc.

The magnetizable pins 40 transport 130 the particle-biomolecule complexes 36 when switched to magnetic and thereby place a bound nucleic acid 28a in a first cavity 20a or in a second cavity 20b with the buffer solution 32a, 32b, etc. Subsequently the magnetizable pins 40 are switched off or the permanently magnetic pins 40 are removed 135.

The transport 130 is optionally followed by a mixing step 140 comprising switching on the counter magnet 50 once or several times. The particle-biomolecule complexes 36 shifts from the switched-off magnetizable pin 40 to the bottom area of the cavity 20.

In a step of mixing 145a, 145b the solution 30 within the cavities 20a, 20b is mixed. The counter magnet 50 is switched off again 146 upon completion of the mixing 145a, 145b.

Of course the plastic covers 42 are disposed on top of the magnetic pins 40, so that the magnetizable pins 40 and the plastic caps 42 dip into the washing buffer solution 32 within the first cavities 20 once or several times.

It would furthermore be possible to carry out the mixing 145a, 145b of the solution 30 or 32a, 32b etc. by alternately switching on and off the counter magnets 50 and the magnetizable pins 40. It is furthermore possible to carry out the mixing 145a, 145b of the solution 30 or 32a, 32b etc. by alternately switching on and off the magnetizable pins 40 and the counter magnets. It is furthermore possible to alternately move the magnetizable pins 40 and the counter magnets 50 up and down. The mixing 145a, 145b of the solution 30 or 32a, 32b is carried out by the particle-biomolecule complex 36 within the solution 30. The mixing 145a, 145b of the solution 30 could also be caused by a movement of the particle-biomolecule complex 36 between a wall area or the bottom area of the first cavity 20a, and the plastic covers 42. Alternatively or additionally the mixing 145a, 145b can be caused by a movement of the particle-biomolecule complexes 36 between the bottom area or the wall area of the second cavity 20b and the plastic covers 42. However, this alternative mixing process is limited by switching cycles of the counter magnets 50 and the magnetizable pins 40.

Switching on 150 the magnetizable pins 40 or inserting the permanently magnetizable pins 40 implemented as the arrangement of permanent magnets (also short referred to as the permanent magnets) collects the particle-biomolecule complex 36 from the washing buffer 32a, 32b again.

In step 160 it is determined whether further washing buffers 32 etc. have to be processed. In case of further washing buffers 32 to be processed, this is followed by the transport 130 to the next cavity 20 with a further washing buffer 32.

However, if according to step 160 no further washing buffers 32 have to be processed, the magnetizable pins 40 and the plastic covers 42 with the particle-biomolecule complex 36 adhering thereto are lifted from the solution 30. A waiting step follows to dry 170 the particle-biomolecule complex 36 at least partially. Subsequently the dried particle-biomolecule complex 36 is transported to the cavity 20 with the elution buffer 33 and is placed 180 in the elution buffer 33. Thereupon the magnetizable pins 40 are switched to non-magnetic or the magnetizable pins 40 implemented as the permanent magnets are removed 190 from the cavities 20.

This is optionally followed by switching on 200 the counter magnet 50, whereby the particle-biomolecule complex 36 increasingly shifts from the switched-off magnetizable pin 40 towards the bottom area of the cavity 20 due to the magnetic field of the counter magnets 50.

In a subsequent step a mixing 210 is carried out in order to dissolve the particle-biomolecule complex 36. The counter magnets 50 are switched off to support a dissolving of the particle-biomolecule complex 36. Further the solution 30 with the elution buffer 33 is mechanically mixed in the cavity 20 within the yield cavity 85 by moving the magnetizable pins 40 up and down in a non-magnetic state (with the magnetic field switched off). Thereby the particle-biomolecule complex 36 is dissolved, the magnetizable particles 35 are brought in suspension and the biomolecules 28 are desorbed from the magnetizable particles 35. The desorbing of the biomolecules 28 is called elution.

A subsequent switching on 220 of the magnetizable pins 40 collects the magnetizable particles 35 which are now freed of the biomolecules 28 from the elution buffer 33. The biomolecules 28 or nucleic acids 28a remain in the elution buffer 33. In addition the residual amount of the magnetizable particles 35 may remain in the eluate, which now comprises the elution buffer 33, the biomolecules 28 or the nucleic acids 28a, and the residual amount of the magnetizable particles 35 which disturb a further processing of the eluate.

The magnetizable particles 35 are removed from the elution buffer 33 by the magnetizable pins 40 switched magnetically. A disposal 240 of the magnetizable particles 35 takes place e.g. into one of the cavities 20 used before with the washing buffer 32a, 32b within the work area 80. The disposal 240 is carried out by switching off the magnetic field. Alternatively the disposal 240 can take place into the receptacle 70 with the magnetizable particles 35 remaining on the magnetizable pins 40.

In a step 245 the residual amount of the magnetizable particles 35 in the elution buffer 33 is pulled downward by switching on 245 the counter magnet 50 of the cavity 20 with the elution buffer 33. The residual amount of the magnetizable particles 35 (i.e. the "residual particles") are thus actively removed from an upper area and are held in the bottom area of the cavity 20. Thereby an ultraclean eluate is yielded in the upper area of the cavity 20 with the eluate 33, containing the purified biomolecules 28 or the purified nucleic acid 28a.

The ultraclean eluate is now removed by pipetting 250 the ultraclean eluate into the cavities 20 within the yield cavity 85 using the pipetting system 840.

To conclude 270 the method 100 the plastic covers 42 on top of the magnetizable pins 40 can be slipped off at the rake above the receptacle 70. If the magnetizable particles 35 remained on the magnetizable pins 40, also the magnetized particles 35 are dropped into the receptacle 70.

The method 100 can purify all types of biomolecules 28 in dependence on the magnetizable particles 35, the lysis buffer 30a, the binding buffers 30b, the washing buffers 32a, 32b and the elution buffers 33. A combination of different biomolecules 28 can be yielded in the purifying with a suitable combination of the washing buffers 32 (32a, 32b, etc.), the elution buffer 33 and a suitable sequence of the method steps. The purifying is possible for DNA and RNA together. Further the purifying is possible for DNA and RNA separately in two cavities within the yield cavity 85, or also in two cavities within two separate yield cavities 85.

This combination of the pipetting technology with a magnet separation via magnetizable transport magnets renders possible an unprecedented repertoire of combined purifications and a greater variability concerning the sample amounts to be processed.

The invention comprises parallel and serial variants of upscaling the sample amount. Upscaling means a targeted increase of a volume of the sample material. The parallel and serial variants of the upscaling can also be combined. Upscaling comprises using several cavities as well as using larger cavities. In the several cavities or the larger cavities the same solution 30 is disposed. The same solution 30 substantially comprises the same sample material, the same buffer solutions and the same magnetizable particles 35. In particular the concentrations and/or the substance amounts are substantially equal for the same solutions 30.

The parallel upscaling is provided by combining the apparatus 10 and the suitable pipetting system 840. A further aspect of the apparatus 10 according to the invention enables a parallel processing of 12 of the samples materials. Of course different numbers of the sample materials are possible. A processing path for the sample materials is referred to as a channel, thus 12 channels are provided. Several of these channels can be used in parallel with one of the sample materials, whereby the volume of the sample material is up to 12 times greater than an initial volume of the sample material. The pipetting system 840 can control a removal of the eluate after a production of the eluate with the elution buffer 33 and the biomolecules 28. The removal can be such that the eluate from the several channels is placed in one or several cavities within the yield cavity 85: The biomolecules 28 that were distributed to individual ones of the several channels are joined again into one or several cavities.

Furthermore the serial upscaling can be achieved for the lysis or the incubation procedure 117 within the lysis cavity 22. An array with several cavities per channel is used as the lysis cavity 22 for the upscaling for the incubation procedure 117. During the method 100 one channel is used several times with the same sample material. At the start, the sample material is distributed to the several cavities of the lysis cavity 22 within one channel. Then the particle-biomolecule complex 36 can be transferred in several steps from the cavities of one channel into the cavity 20 within the work plate 80. The cavity 20 comprises the first washing buffer 32a.

The serial upscaling can achieve a multiple, for example, up to a five-fold sample amount, within one channel. The five-fold sample amount is an upper limit for the serial upscaling. The upper limit results from a capacity of the washing buffers. The washing buffers can be loaded with up to the five-fold amount of the magnetizable particles 35 used in one individual isolation process. Consequently the sample volume could be increased by 96-fold when combining the serial upscaling within the several channels and the parallel upscaling of several parallel channels. The upper limit of the 96-fold is reachable when using a 96-cavity microtiter plate. This means, starting from a usual sample volume of 0.2 ml, in the extreme case more than 10 ml of the sample material could be purified. The sample volume of 10 ml is the amount which is at most contained in, for example, a standard collection cavity for blood or serum. However, per run only one of the sample materials can be processed when combining the parallel upscaling and the serial upscaling. No change in equipment is required for the combining of the parallel and the serial upscaling. A conventional 96-cavity microtitter plates may be used together with the plastic covers 42.

FIG. 3a shows an aspect of a plate with incubator cavities 65. The plate shown in FIG. 3a with the incubator cavities 65 is the conventional multiwell plate. The incubator cavities 65 can accommodate the sample volume greater than 2 ml. The incubator cavities 65 of the multiwell plate can furthermore be arranged in the apparatus 10 along a working direction of the apparatus 10. The working direction of the apparatus 10 preferably corresponds to the longitudinal direction (x direction) for moving the frame 45.

FIG. 3b shows an aspect of the lysis cavity 22 that can also be used as the work plate 80. Preferably the lysis cavity 22 and/or the work plate 80 are exchangeable plates, e.g. the 96-cavity microtiter plates or the deepwell plates. The deepwell plates are available as disposable articles. Usually the 96-cavity microtiter plate comprises eight rows (A . . . H) of respectively twelve (1 . . . 12) cavities 65. Of course also different numbers of the rows and the columns are possible. Furthermore non-orthogonal arrays of the cavities 65 or 20 are possible.

There are several alternative ways for the serial upscaling to take place within one of the several channels in the incubation unit 60. Additionally a special plate is used with voluminous incubator cavities 65. The voluminous incubator cavities 65 comprise the sample volume of e.g. larger than 10 ml. FIG. 3a shows an example of the voluminous incubator cavities 65, i.e. elongated incubator cavities 65. The magnetizable particles 35 are placed into the voluminous incubator cavities 65. The magnetizable particles 35 are collected from the voluminous incubator cavities 65 after adsorbing the biomolecules 28 using the magnetic field of the magnetizable pins 40.

Optionally the transfer of the collected magnetizable particles 35 from the lysis cavity 22 into the work plate 80 can also take place in several sequential steps. Alternatively a lysis cavity 22 with numerous cavities 20 of a usual size (approx. 1 to 2 ml) can be used e.g. the 96-cavity microtiter plate or the deepwell plate. Then, a mixture of the sample material and the reagents is distributed to several cavities 65 of the lysis cavity 22. The magnetizable particles 35 are first placed into at least one of the several cavities 65. Subsequently, starting with a first filled cavity, the magnetizable particles 35 are sequentially transferred to all of the several cavities filled with the mixture. The magnetizable particles 35 increasingly take up the biomolecules 28 from all the several cavities. At the end the apparatus 10 has collected the biomolecules 28 from all the several cavities 65 of the lysis cavity 22. The collected biomolecules 28 are transferred to a first cavity on the work plate 80.

In a further variant of the serial and the parallel upscaling several of the parallel channels (e.g. 1 ... 12) each comprising the several cavities 65 (e.g. A-H) of the lysis cavity 22 are filled with the same sample material. Processing steps are executed one by one, from the incubating to an extracting up to finalizing the eluate in to one cavity of the work plate 80; preferably a last cavity on the work plate 80. For more than one of the channels a last row of the cavities comprising the eluate is formed. The eluate can be transferred from the last row of the cavities into at least one cavity on the yield cavity 85 using the pipetting system 840.

The invention furthermore provides that the magnetizable pins 40 are not only movable in the vertical z direction but additionally along the longitudinal x direction of the apparatus 10. The longitudinal movement of the magnetizable pins 40 may be of interest for the mixing of the solutions 30 within the lysis cavity 22 with the voluminous cavities 20 extending in the longitudinal direction of the apparatus 10, such as the incubator cavities 65 shown in FIG. 3a. The magnetizable pins 40 can also be moved in an oscillating fashion up and down in the vertical z direction and/or back and forth in the longitudinal direction of the apparatus 10.

FIG. 3c first shows the process steps without the upscaling. The particle-biomolecule complex 36 is transferred out of the lysis cavity 22 to individual ones of the cavities 20a, 20b of the work plate, as already described.

FIG. 3d shows a first variant of the serial upscaling from the incubator cavity 65 of the incubation plate, as shown in FIG. 3b. The particle-biomolecule complex 36 is collected from the incubator cavity 65 by moving the plastic covers 42 with the magnetizable pin 40 in the x direction and the z direction. The particle-biomolecule complex 36 is transported 130 into the first cavity 20a of the work plate 80.

FIG. 3e shows a further variant of the upscaling from a standard plate as the lysis cavity 22 into the work plate 80 formed by a standard plate. It is possible to transport the magnetizable particles 35 from left to right through the rows A, B, C, . . . H. Upon each contact of the magnetizable particles 35 with the solutions 30 in the lysis cavity 22 a yield of the biomolecules 28 is increased. The biomolecules 28 forming the particle-biomolecule complex 36 are bound to the magnetizable pins 40. The biomolecules 28 are thus extracted from the lysis cavity 22. A transfer of the particle-biomolecule complex 36 takes place in one single transport step 130 in this variant of the upscaling from the standard plate.

FIG. 3f shows yet a further variant of the upscaling from the standard plate forming the lysis cavity 22 into the work plate 80. The work plate 80 comprises the standard plate as with FIG. 3e. In FIG. 3f not all rows of the lysis cavity 22 are passed sequentially in contrast to FIG. 3e. An individual transport 130 of the particle-biomolecule complexes 36 takes place from each one of the rows A, B, C, . . . H into the first cavity 20a of the working plate 80, instead.

FIGS. 4a to 4c and 5a and 5b show an alternative aspect of the apparatus 10. The incubation unit 60 in the alternative apparatus 10 is substantially bigger than in FIG. 1a-1c, so that the voluminous incubator cavities 65 shown in FIG. 3a can be accommodated in the incubation unit 60. Furthermore the yield area 86 is no longer arranged on the apparatus 10. The yield area 86 in the alternative aspect of the apparatus 10 forms part of the system 800, as will be explained below.

A lid 61 of the incubation unit 60 is designed in such that the lid 61 can be opened automatically, e.g. using a hinge. In FIG. 4a the lid 61 is shown in a closed state. The lid 61 furthermore optionally has small openings 62 for inserting the magnetizable pins 40. The frame 45 can be moved across the incubation unit 60 when the lid 61 is closed and when the lid 61 is opened, so that the magnetizable pins 40 have access to the incubator cavities 65. On the frame 45 a drip-catcher 46 is arranged that is best seen in FIGS. 4a and 4c. The drip-catcher 46 moves underneath the tips 41 of the magnetizable pins 40, whereby a contamination of the cavities 20 by a dripping from the magnetizable pins 40 is prevented.

A first drive unit a comprising, for example, the first drive motor 90a and the first band 92a moves the sliding carriage or the frame 45 in the x direction. The second drive unit b, comprising, for example, the second drive motor 90b and the second band 92b, opens and closes the lid 61 of the incubation unit 60. A third drive unit c, with, for example, a motor 90c, moves the magnetizable pins 40. The magnetizable pins 40 may comprise the permanent magnets and the electromagnets as is explained below. The plastic covers 42 are arranged on top of the magnetizable pins 40 vertically in the z direction. A fourth drive unit 90d serves to move the counter magnets 50.

The third drive unit 90c comprises e.g. a simple motor drive that moves the magnetizable pins 40 up and down in the z direction for the aspect of the magnetizable pins 40 using the electromagnets. The magnetic field is then switched on and off electrically.

The third drive unit 90c comprises two motors, wherein at least a magnetically effective portion of a permanently magnetic arrangement can be removed from the cavities 20 for the aspect of the magnetizable pins 40 using the permanently magnetic arrangements. The permanently magnetic arrangements are moveable far enough from the cavities 20, so that the cavities 20 are no longer exposed to the magnetic field of the magnetizable pins 40. Hence, the magnetic field of the magnetizable pins 40 is effectively switched off.

FIG. 4d shows a further aspect of the magnetizable pin 40 of the apparatus 10 in a cross section. The magnetizable pin 40 comprises a mantle 40a. On the mantle 40a the plastic cover 42 is disposed approximately in a lower third. The plastic cover 42 provides a tip 41 of the magnetizable pin 40. By changing the plastic cover 42 it is possible to ensure the cleanliness of the tip 41 in a simple manner. The bulge 43 of the magnetizable pins 40 (see. FIGS. 1a-1c) can be omitted in the further aspect of the magnetizable pin 40.

The further aspect of the magnetizable pin 40 furthermore comprises a retaining clip 40g. The retaining clip 40g serves to hold the plastic cover 42 on the mantle 40a of the magnetizable pin 40. The retaining clip 40g connects the plastic cover 42 in a detachable fashion with the mantle 40a of the magnetizable pin 40. Therefore the plastic covers 42 can be taken up by the mantle 40a and can be shed again reliably.

Dimensions of the mantle 40a and of the plastic cover 42 can be adjusted such that a positive fit of the plastic cover 42 on the mantle 40a of the magnetizable pin 40 is achieved. The positive fit is an alternative to the detachable connection of the plastic cover 42 to the mantle 40a using the retaining clip 40g.

On the inside of the mantle 40a a hollow 40b is disposed. The hollow 40b is adapted to accommodate a magnetizable element. The hollow 40b and consequently the magnetizable element can be moved along the longitudinal axis of the magnetizable pin 40 indicated by a dashed line. The mobility of the magnetizable element serves to control the effect of the magnetizable element on the tip 41 of the magnetizable pin 40.

If the magnetizable element is disposed in the area of the tip 41, the tip 41 is magnetized. This state of the magnetizable element is also referred to as "switching on of the magnetizable pin 40". If the magnetizable element is disposed at a distance from the tip 41, the tip 41 is not magnetized. This state of the magnetizable element is also referred to as "switching off of the magnetizable pin 40". A change is possible between switching on and switching off the magnetizable pin 40 by moving the magnetizable element between the tip 41 and a position at the distance from the tip 41. A speed of the change determines a frequency of the change of the magnetization of the tip 41. The magnetizable element in the hollow 41 can be implemented either as the permanent magnet or as the electromagnet. Electric conductors to the magnetizable element in the hollow 40b and a corresponding voltage supply are required for electromagnets in the hollow 40b.

It is furthermore conceivable to combine the permanent magnets and the electromagnets within the magnetizable element. Thus the electromagnet could be supplied with the current flow such that the magnetic field of the electromagnet is opposed to and in total greater than the magnetic field of the permanent magnet. Such an aspect of the magnetizable element would be of interest if a magnetic pulse was used to detach the biomolecules 28 or the particle-biomolecule complex 36 from the magnetizable pin 40.

If the magnetizable element is implemented exclusively as the electromagnet, furthermore the mobility of the magnetizable element in the hollow 40b relative to the mantle 40a of the magnetizable pin 40 can be omitted.

An aspect of the magnetizable pin 40 shown in FIG. 4d allows a movement of the mantle 40a independent from a movement of the hollow 40b. Consequently, even if the permanent magnet is used as the magnetizable element in the hollow 40b, the magnetizable pins 40 can be lowered into the cavities 20 in the switched-off state.

The apparatus 10 has only two axes (x direction longitudinal and z direction vertical) and does not allow any translations in the lateral y direction. However, the suitable pipetting system 840 having at least three axes allows the parallel and serial upscaling as described above.

The invention furthermore provides a system 800 for diagnostically purifying biomolecules 28. The diagnostically purifying of the biomolecules 28 means that regulations and directives of in-vitro diagnostics (IVD) are fulfilled. The system 800 ensures that a user of the system 800 cannot cause a confusion of the sample materials and substances. Moreover all steps carried out by the system 800 are comprehensively recorded.

FIG. 5a shows a top view of the system 800 according to the present invention. The system 800 comprises the apparatus 10 according to the present invention for purifying biomolecules 28. The apparatus 10 contains the incubation unit 60 and furthermore the elements of the apparatus 10 already discussed above. The elements of the apparatus 10 are only provided with reference numerals in the FIGS. 5a and 5b if relevant for the description of the system 800. Concerning all other elements of the apparatus 10 reference is made to the FIGS. 1a-1c and FIGS. 4a-4c.

The system 800 comprises a loading bay 600 for accommodating the substances in the system 800 in addition to the apparatus 10. The system 800 furthermore comprises a control unit 860 for controlling the system 800 and the method steps carried out by the system 800. The system 800 furthermore comprises the suitable pipetting system 840. The suitable pipetting system 840 is shown in a perspective view in FIG. 5b. The pipetting system 840 can be moved above the system 800 and can sweep a base surface of the system 800. The pipetting system 840 is suitable to transfer the substances from the loading bay 600 into the apparatus 10 and/or from the apparatus 10 to the yield area 85. Required pipetting tips are automatically taken up from a storage cavity 880.

In the system 800 the yield area 85 was shifted from the apparatus 10 to an area which is disposed in front of the apparatus 10. This means that the eluate can be transferred directly into the yield area or into a yield cavity 85 using the pipetting system 840.

The loading bay 600 comprises a number of sample receptacles 610 to accommodate sample cavities 620 (best visible in FIG. 7b). The sample cavities 620 are identified 1031 using a reading device 500 upon the sample cavities 620 being placed 1030 into the loading bay 600 of the system 800. The reading device 500 may comprise a barcode reader.

The system 800 comprises a detection unit 870 for detecting coded information about the substances. The substances are the sample materials, comprising liquids and solids that are used in a course of the method 100 in the apparatus. The detecting comprises the recognition of at least one coding.

In a simplest case only the sample coding is detected in order to transfer the sample coding to the yield cavity unaltered and error-free at an end of the purifying.

In an alternative aspect the detection comprises recognizing a coding of the substances within the loading bay 600, e.g. via barcodes. The alternative aspect is of interest with respect to components of a kit for the purifying of the biomolecules 28. A check for consistency can be carried out in order to rule out any confusion of the substances and reagents within the kit. Furthermore the check for consistency can check if a correct kit is being used for the purifying of the biomolecules 28.

As a further alternative of an identifying 1031 of the sample material can take place automatically. A selection of method steps to be executed can be derived based upon the coding. Furthermore a selection of the substances can be derived for the substances required for an execution of the method 100. An information system may be used upon deriving the selection of the method steps and the selection of the substances. The system 800 is adapted to identify 1031 the sample cavities 620 and a content of the sample cavity 620 using the reading device 500.

An alternative detection variant can determine properties of the cavities and containers used. A cross section of the sample cavity 620 can be determined by a position of the sample cavity 620 in the system 800. The cross section results from the cross section of a cylindrical opening in that the sample cavity 620 is inserted. A height of the sample cavity 620 and consequently a volume of the sample cavity 620 can be coded on a reading element 501, so that the volume of the sample cavity 620 becomes part of identifying 510 the sample cavity 620 and the sample material.

The loading bay 600 furthermore comprises a row of substance receptacles 650. The substance receptacles 650 comprise cylindrical openings of different sizes, into which the substance cavities 630 (not shown) can be inserted. A position of the substance cavity 630 is determined upon inserting or pushing 1035 the substance cavities 630 into the loading bay 600 and thereby a cross section is known for the substance cavity 630. Furthermore a content of the substance cavity 620 is identified 1036 from the reading element 501 by the reading device 500. The height of the substance cavity 620 can also be coded on the reading element 501. This is of interest for placing 630 the substance cavities 620 of different heights in the loading bay 600.

It is conceivable that the sample material is placed 1035 into the system 800 in one of the substance receptacles 650 when a large amount of the sample material has to be purified. The reading device 500 will correctly identify 1031 the sample material placed in one of the substance receptacles 650.

The system 800 furthermore optionally comprises a plurality of sensors 830 to record and log a plurality of parameters 835. The plurality of parameters 835 comprises the temperature of the incubation unit 60 and a dwell time of the sample material in the incubation unit 60. The plurality of parameters is not limited to the above examples. Furthermore a plurality of parameter controls 839 is provided to control the plurality of parameter values in the system 800.

The system 800 is adapted to determine at least one buffer solution. The at least one buffer solution comprises at least one binding buffer 30b. The system 800 is further adapted to determine the washing buffers 32 and the elution buffers 33 as well as the magnetizable particles 35, required for the execution of the method 100 based on the identified sample material as described above. Furthermore the system 800 is adapted to determine a required substance amount for each of the elements of the substances and the reagents. It is possible to determine the process parameters on the basis of the substances placed in the apparatus 10 and to control the apparatus 10 and the method steps, based on the identification of the substances without interpreting the coding of the sample material.

The system 800 is furthermore adapted to determine a particular IVD-conforming sequence of the method steps. The determination can be based on at least one of the identified sample material substances and the reagents used and further process parameters for the diagnostically purifying of the biomolecules 28. The system 800 is furthermore adapted to determine a required form of documentation for the diagnostically purifying of the biomolecules 28. Likewise the number of the method steps required for the diagnostically purifying and a selection of the substances and the reagents, can be determined (e.g. the type of magnetizable particles 35) on the basis of the detected information.

FIG. 5b shows a perspective view of the system 800 according to the invention. In this representation the sample cavities 620 are particularly easily recognizable.

FIG. 6a shows an extension of the method 100 carried out as a method 900 for a diagnostically purifying of biomolecules 28. The method 900 extends the method 100 of FIG. 2.

More specifically, FIG. 6a shows an extension of the step 102 of taking up the plastic covers 42 on the magnetizable pins 40 in the method 100. Step 102 has to be expanded, if the method 900 is to be executed.

In a step 1005 first a plate with incubator cavities 65 is loaded into the incubation unit 60. Subsequently in a step 1010 first a work plate 80 is loaded into the work-plate accommodation 81 of the apparatus 10.

This is followed by a step 1012 to check whether the plastic covers 42 have to be refilled in the racks 44. In case a refill is necessary, the racks 44 are refilled in a step 1015.

Subsequently in a step 1020 the work plate 80 is loaded with the required elution buffers 33 and/or the washing buffers 32. Finally it is checked in a step 1021 whether the receptacle 70 for the disposables needs to be emptied. If required, the emptying is carried out with a step 1025.

In a step 1030 the sample cavities 620 are placed into the loading bay 600. Therein the identification of the inserted sample cavities takes place in a step 1031. Subsequently in a step 1035 the substance cavities 630 are placed into the loading bay 600, whereupon the inserted substance cavities 630 are identified in step 1036.

The system 800 determines in step 1040 a suitable multiwell plate and loads the suitable multiwell plate into the incubation unit 60 based on the identified sample material and/or the identified substances. In the step 1040 a required incubation volume is taken into account.

In a step 1045 the information read by the reading device 500 is recorded and transmitted to the control unit 860 and/or the documentation unit 850. Furthermore the step 1045 allows a consistency check of the identified substances in the loading bay 600. Thereby for example the use of a false buffer solution with the sample material can be prevented, so that falsely positive or falsely negative results can be prevented for the diagnostically purifying.

In a step 1050 required process parameters 850 are determined

FIG. 6b shows the individual stages of the step 1050. First in a step 1055 required substances are determined among the identified substances in the loading bay 600. Subsequently in a step 1060 a substance amount is determined for each of the required substances in order to carry out the method 900. The substances used in the method 900 are at least one element of the substances and the reagents discussed above.

In a step 1065 parameter values 835 are determined based on the identified substances. This is followed by a step 1070 in which the required process steps are determined on the basis of the identified substances.

Subsequently in step 1075 the apparatus 10 is controlled by the control unit 860 of the system 800. The control unit 860 monitors the apparatus 10 during the execution of the method 900. The step 1075 also comprises a monitoring of the parameter values 835 during the execution of the method 900.

If the method 900 is carried out, the step 105 (FIG. 2) for supplying the sample material can be omitted, since the sample material was already supplied in step 1030 (FIG. 6a).

FIG. 7 shows a block diagram of the system 800 according to the invention. The system 800 comprises a parameter control 839 to control the plurality of parameter values 835. The parameter values 835 are detected by a plurality of sensors 830. Furthermore the system 800 comprises the apparatus 10 according to the invention, the pipetting system 840 as well as a documentation unit 850. The documentation unit 850 is adapted for documenting detected information, for example information read by the reading device 500. The information read by the reading device 500 is recorded in a recording module 870 and forwarded to the system control 860 and/or the documentation unit 820. The control unit 860 controls and regulates the system 800 on the basis of programs and the recognized information about the substances. The elements of the system 800 shown in FIG. 7 are connected to each other and communicate with each other.

The system 800 comprises software for controlling the method 900 shown in FIGS. 6a and 6b. The software is run by a microprocessor and can be programmed in any suitable programming language.

The invention claimed is:

1. A system for diagnostically purifying biomolecules comprising:
   a plurality of cavities for accommodating solutions, the plurality of cavities comprising at least one sample cavity for a sample material, wherein the sample material comprises the biomolecules and wherein the sample cavity bears an unambiguous identification, at least one yield cavity, and at least one of a lysis cavity, one or more washing cavities and an elution cavity,
   at least one movable and magnetizable pin arranged in such a fashion that the movable and magnetizable pin can be inserted in at least one of the lysis cavity, in the one or more washing cavities and in the elution cavity,
   a control unit for controlling the system,
   magnetizable particles to which the biomolecules are attachable to form a particle-biomolecule complex
wherein the system yields an eluate with the diagnostically purified biomolecules from the sample material by transporting the particle-biomolecule complex with the at least one movable and magnetizable pin to at least the elution cavity wherein the biomolecules are desorbed from the magnetizable particles, and
   a coding detection and transfer unit for the unambiguous identification of a coding relating to the content of the sample material in the at least one sample cavity and for reallocating the coding to the result in the at least one yield cavity.

2. The system according to claim 1 furthermore comprising:
   a loading bay for accommodating substances, wherein the substances are at least one of the sample material, a buffer solution or the magnetizable particles,
   a reading module for automatically identifying the substances and the sample material upon accommodating in the loading bay,
   an incubation unit for heating, thermostating and incubating the samples in the lysis cavity,
   a pipetting unit for transferring the substances,
   a receptacle.

3. The system according to claim 1, furthermore comprising:
   apparatus for improving the quality of the eluate before removing by pipetting adapted to keep the magnetizable particles away from a tip of the pipetting device.

4. The system according to claim 1, furthermore comprising:
   sensors for recording and logging a plurality of parameters using a documentation unit.

5. The system according to claims 1, furthermore comprising:
   a plurality of parameter controls for controlling the plurality of parameters using the control unit.

6. The system according to claim 2, wherein the control unit is adapted to check a consistency of the substances disposed in the loading bay based on the substances in the loading bay.

7. The system according to claim 6, wherein the control unit is adapted to check, if the consistency of the substances disposed in the loading bay is correct based on a composition of a kit.

8. The system according to claim 6, wherein the control unit is adapted to output a message in the case that the consistency of the substances in the loading bay is not correct.

9. The system according to claim 6, wherein the control unit is adapted to prevent an opening of the loading bay during the controlling of the system, in case that the consistency of the substances disposed in the loading bay is correct.

10. The system according to claim 2, wherein the system is adapted to determine a substance amount of required buffer solutions in the loading bay based on the identified substance in the loading bay.

11. The system according to claim 2, wherein the system is adapted to determine a substance amount of the required magnetizable particles based on the identified substance in the loading bay.

12. The system according to claim 2, wherein the system is adapted such that the system determines a number and a sequence of process steps of a method for diagnostically purifying biomolecules based on the identified substance in the loading bay.

13. The system according to claim 2, wherein the system is adapted to determine an appropriate incubation volume for incubating based on the identified substance in the loading bay.

14. The system according to claim 13, wherein the system is adapted to determine a suitable multiwell plate for incubating based on the appropriate incubation volume.

15. The system according to claims 1, wherein the system is adapted to automatically select, request and use at least one suitable cavity from the group consisting of lysis cavity, incubator cavity, work plate, cavity of the work plate, yield plate.

* * * * *